United States Patent
Sidransky

(10) Patent No.: US 8,617,809 B2
(45) Date of Patent: Dec. 31, 2013

(54) NEOPLASIA SCREENING COMPOSITIONS AND METHODS OF USE

(75) Inventor: David Sidransky, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 604 days.

(21) Appl. No.: 11/884,406

(22) PCT Filed: Feb. 14, 2006

(86) PCT No.: PCT/US2006/005299
§ 371 (c)(1),
(2), (4) Date: Sep. 5, 2008

(87) PCT Pub. No.: WO2006/088940
PCT Pub. Date: Aug. 24, 2006

(65) Prior Publication Data
US 2009/0054260 A1 Feb. 26, 2009

Related U.S. Application Data

(60) Provisional application No. 60/652,594, filed on Feb. 14, 2005, provisional application No. 60/652,591, filed on Feb. 14, 2005, provisional application No. 60/652,590, filed on Feb. 14, 2005, provisional application No. 60/653,295, filed on Feb. 16, 2005.

(51) Int. Cl.
*C12Q 1/68* (2006.01)
*A61K 49/00* (2006.01)

(52) U.S. Cl.
USPC ............ 435/6.1; 435/6.14; 435/7.23; 424/9.1

(58) Field of Classification Search
None
See application file for complete search history.

(56) References Cited

FOREIGN PATENT DOCUMENTS

WO    WO-01/75172    10/2001

OTHER PUBLICATIONS

Valenzuela, MT et al. Assessing the use of p16 promoter gene methylation in serum for detection of bladder cancer. 2002. European Urology. vol. 42 pp. 622-630.*
Feng, Suhua et al. Conservation and divergence of methylation patterning in plants and animals. PNAS 2010 vol. 107 No. 19 pp. 8689-8694).*
Thisted What is a P value? The University of Chicago 1998 http://www.stat.uchicago.edu/~thisted.*
Tada, Yasuhiro et al. The association of death-associated protein kinase hypermethylation with early recurrence in superficial bladder cancers. Cancer Research 2002 vol. 62 pp. 4048-4053.*
Chan, Michael et al. Hypermethylation of mulifple geens in tumor tissues and voided urine in urinary bladder cancer patients. Clinical Cancer Research 2002 vol. 8 pp. 464-470.*
Esteller, Manel et al. Inactivation of the DNA repair gene O6-methylguanine-DNA methyltransferase by promoter hypermethylation is a common even in primary human neoplasia. Cancer Research 1999 vol. 59 pp. 793-797.*
Maruyama, Riichiroch et al. Aberrant promoter mehtylation profile of bladder cancer and its relationship to clinicopathological features. Cancer Research 2001 vol. 61 pp. 8659-8663.*
Dominguez, Gemma et al. Prevalence of aberrant methylation of p14ARF over p16INK4a in some human primary tumors. 2003 Mutation Research vol. 530 pp. 9-17.*
Lo et al. (1999) Quantitative Analysis of Aberrant p16 Methylation Using Real-Time Quantitative Methylation-specific Polymerase Chain Reaction. Cancer Research, 59:3899-3903.*
Li et al. (2002) MethPrimer: designing primers for methylation PCRs. Bioinformatics, 18(11):1427-1431.*
GenBank record NM_016152, GI: 7706624, *Homo sapiens* retinoic acid receptor, beta (RARB), mRNA. Feb. 3, 2001. Accessed from: <http://www.ncbi.nlm.nih.gov/nuccore/7706624?sat=8 &satkey=1892732> on Sep. 4, 2012. Three pages.*
Chan et al., "Frequent Hypermethylation of Promoter Region of Rassfia in Tumor Tissues and Voided Urine of Urinary Bladder Cancer Patients," Int. J. Cancer (2003), 104:611-616.
Dulaimi et al., "Detection of Bladder Cancer in Urine by a Tumor Suppressor Gene Hypermethylation Panel," Clinical Cancer Research (2004), 10:1887-1893.
Esteller et al., "A Gene Hypermethylation Profile of Human Cancer," Cancer Research (2001), 61:3225-3229.
Maruyama et al., "Aberrant Promoter Methylation Profile of Bladder Cancer and Its Relationship to Clinicopathological Features," Cancer Research (2001), 61:8659-8663.
Tada et al., "The Association of Death-associated Protein Kinase Hypermethylation with Early Recurrence in Superficial Bladder Cancers," Cancer Research (2002), 62:4048-4053.
"Affymetrix GeneChip Human Genome U133 Plus 2.0 Array," GEO Expression, Nov. 7, 2003, XP-002361326.
European Search Report, for related Appl. No. EP06720773.8, dated Dec. 8, 2009.
Valenzuela et al., "Assessing the use of p16(INK4a) promoter gene methylation in serum for detection of bladder cancer." Eur Urol. Dec. 2002;42(6):622-8; discussion 628-30.

* cited by examiner

*Primary Examiner* — Anne Gussow
*Assistant Examiner* — Neil P Hammell
(74) *Attorney, Agent, or Firm* — Johns Hopkins Technology Transfer

(57) ABSTRACT

As described in more detail below, the present invention generally features compositions and non-invasive methods useful for the screening, identification, monitoring, or diagnosis of subjects having a neoplasia. The invention further provides highly accurate non-invasive methods for the staging or selection of treatment for a bladder, renal, or prostate cancer in a subject.

6 Claims, 13 Drawing Sheets

Figure 1: Fifteen paired tumor and urine DNA samples

SUMMARY OF METHYLATION STATES OF GSTP1, ARF, MGMT, RARβ2, TIMP3, CDH1, APC, AND RASSF1A IN 17 PRIMARY TUMORS (T) AND MATCHED URINE (U) AND SERUM (S) SAMPLES. BLACK BOXES REPRESENT SAMPLES THAT ARE METHYLATED; WHITE BOXES REPRESENT SAMPLES WITHOUT METHYLATION.

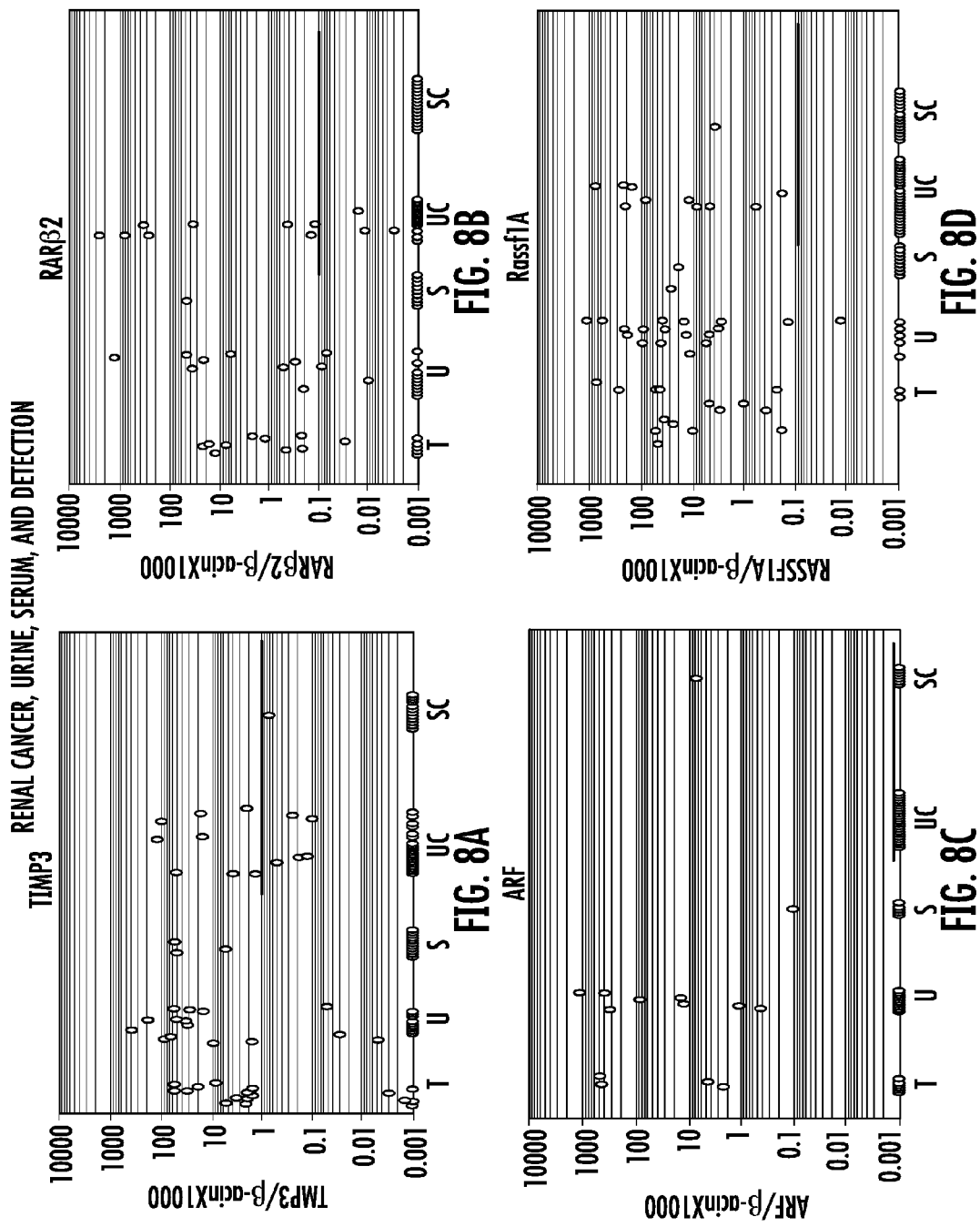

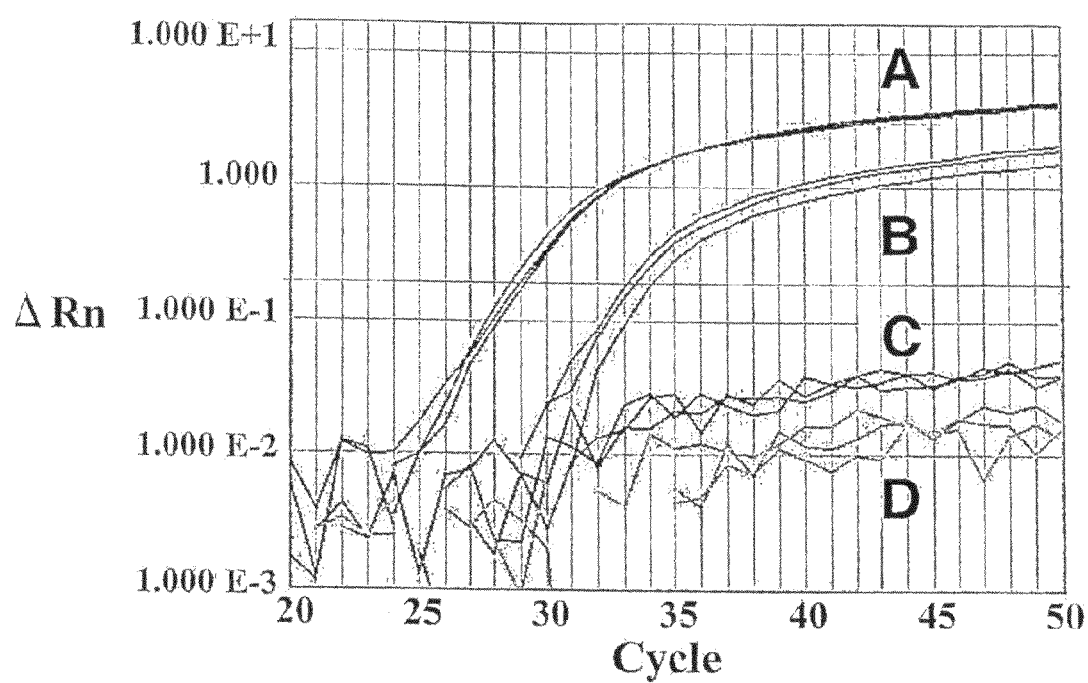
Example 3: Figure 9

NEOPLASIA SCREENING COMPOSITIONS AND METHODS OF USE

CROSS-REFERENCE TO RELATED APPLICATION

This application claims the benefit of the following U.S. Provisional Application Nos. 60/652,594, which was filed on Feb. 14, 2005; 60/653,295, which was filed on Feb. 16, 2005; 60/652,591, which was filed on Feb. 14, 2005; and 60/652,590, which was filed on Feb. 14, 2005; each of which is hereby incorporated by reference in their entirety.

BACKGROUND OF THE INVENTION

Neoplasias, including bladder, renal, and prostate cancers, are a significant cause of human morbidity and mortality. Bladder cancer is the fourth most common cancer in men and the eighth in women both in terms of incidence and mortality; renal cancer kills approximately 12,000 Americans every year, and 30,000 new cases of renal cancer are reported each year in the United States; and prostate cancer is clinically diagnosed in one of every 11 American men. One third of men diagnosed will prostate cancer will develop a life threatening disease In their earliest stages, bladder, renal, and prostate neoplasias are clinically silent. When and if clinical symptoms do develop, patient diagnosis typically involves invasive procedures that lack sensitivity and accuracy. Highly reliable, noninvasive screening methods would permit patient screening, diagnosis, and prognostic evaluation. In addition, such methods would be useful for monitoring patients during or after cancer therapy.

SUMMARY OF THE INVENTION

As described in more detail below, the present invention generally features compositions and methods useful for the screening, diagnosis, staging, and monitoring of subjects for a neoplasia, such as bladder, renal, or prostate cancer. Advantageously, the biological samples used in the methods of the invention are obtained using non-invasive means.

In general, the invention provides methods for bladder, renal, or prostate neoplasia subject screening, diagnostic or prognostic evaluation, tumor staging and patient monitoring. The method comprises determining the methylation level of at least one (e.g., one two, three, four, five, six, seven, eight, nine, ten, eleven) promoter, such as pi-class glutathione S-transferase (GSTP1), O6-methylguanine DNA methyltransferase (MGMT), p14/ARF, (ARF) p16/INK4 a (p16), RAS-associated domain family 1A (RASSF1A), adenomatous polyposis coli (APC), tissue inhibitor of metalloproteinase-3 (TIMP3), or retinoic acid receptor β2 (RARβ2), E-cadherin (CDH1), or Tazarotene-induced gene 1 (TIG1), LOXL1, LOXL4), in a biological sample, wherein the promoter methylation level correlates with the presence, absence, or stage of a neoplasia in the subject; and comparing the methylation level at the promoter with a reference, wherein an alteration (e.g., an increase or decrease) in promoter methylation level identifies, provides a diagnostic or prognostic evaluation, tumor staging, or patient monitoring of a bladder, renal, or prostate neoplasia.

In one aspect, the invention provides a method for identifying a subject having a bladder neoplasia. The method involves determining the promoter methylation of at least one promoter in a biological sample from the subject, where an increase in promoter methylation in the sample relative to a reference identifies the subject as having a bladder neoplasia.

In another aspect, the invention provides a method of diagnosing a subject (e.g., a human patient suspected of having a bladder neoplasia) as having a bladder neoplasia. The method involves determining the promoter methylation of at least one promoter in a biological sample from the subject, where an increase in promoter methylation in the sample relative to a reference identifies the subject as having a bladder neoplasia.

In yet another aspect, the invention provides a method of monitoring a subject diagnosed as having a neoplasia. The method involves determining the methylation of a promoter, where an altered level (e.g., increased or decreased) of promoter methylation relative to the level of methylation in a reference indicates an altered severity of neoplasia in the subject. In one embodiment, the method is used to detect the recurrence of a bladder neoplasia in a subject currently undergoing treatment or previously treated for bladder neoplasia.

In yet another aspect, the invention provides method of determining bladder neoplasia stage in a subject. The method involves determining the promoter methylation of at least one promoter in a biological sample from the subject, where an altered (e.g., increased or decreased) level of promoter methylation in the sample relative to a reference indicates the bladder neoplasia stage in the subject. In one embodiment, ARF and MGMT methylation correlate with increasing tumor (T) stage.

In yet another aspect, the invention provides a method of determining the clinical aggressiveness of a bladder neoplasia in a subject. The method involves determining the promoter methylation of at least one promoter in a biological sample from the subject, where an altered level (e.g., increased or decreased) of promoter methylation in the sample relative to a reference level indicates an increased clinical aggressiveness of bladder neoplasia. In one embodiment, ARE, GSTP1, or TIMP3 methylation correlate with an increase in tumor invasiveness.

In yet another aspect, the invention provides a method of selecting a treatment for a subject diagnosed as having a bladder neoplasia. The method involves (a) determining an altered level (e.g., increased or decreased) of methylation of a promoter in a biological sample from the subject; and (b) selecting a treatment for the subject, where the treatment is selected from the group consisting of surgery, chemotherapy, biological therapy, and radiotherapy. In one embodiment, an increase in ARF, GSTP1, TIMP3, and MGMT promoter methylation indicates that more aggressive therapy is appropriate. In one embodiment, an increase in p16, ARF, MGMT, and GSTP1 promoter methylation indicates that more aggressive therapy is appropriate.

In yet another aspect, the invention provides a method of determining the prognosis of a subject diagnosed as having a bladder neoplasia. The method involves determining the methylation of a promoter in a biological sample from the subject, where an altered (e.g., increased or decreased) level of promoter methylation relative to a reference indicates the prognosis of the subject. In one embodiment, an increased level of promoter methylation indicates a poor prognosis and a decreased level of promoter methylation indicates a good prognosis. In another embodiment, an increase in ARF, GSTP1, TIMP3, or MGMT promoter methylation indicates a poor prognosis.

In yet another aspect, the invention provides a method for detecting bladder neoplasia in a biological sample. The method involves determining the methylation of a promoter selected from the group consisting of p16, ARF, GSTP1, MGMT, RAR-β2, TIMP3, CDH1, RASSF1A, and APC in the biological sample, where an increase in promoter methylation relative to a reference indicates the presence of bladder neoplasia in the biological sample. In one embodiment, the biological sample is a tissue sample.

In yet another aspect, the invention provides a method for determining the methylation profile of a bladder neoplasia. The method involves determining the methylation of a promoter selected from the group consisting of p16, ARF, GSTP1, MGMT, RAR-β2, TIMP3, CDH1, RASSF1A, and APC in a biological sample, where the level of promoter methylation relative to a reference determines the methylation profile of the bladder neoplasia.

In yet another aspect, the invention provides a kit for determining promoter methylation, the kit containing at least one nucleic acid molecule capable of binding selectively to a methylated or unmethylated promoter sequence and directions for using the nucleic acid molecule for the analysis of promoter methylation. In one embodiment, the promoter is selected from the group consisting of p16, ARF, GSTP1, MGMT, RAR-β2, TIMP3, CDH1, RASSF1A, and APC.

In yet another aspect, the invention provides a kit for determining promoter methylation, the kit containing at least one pair of primers capable of amplifying a promoter sequence selected from the group consisting of p16, ARF, GSTP1, MGMT, RAR-β2, TIMP3, CDH1, RASSF1A, and APC, where at least one of the primers binds selectively to a methylated or unmethylated sequence.

In embodiments of the previous aspects, the kit further includes directions for the use of the kit in identifying the presence of a bladder neoplasia in a subject. In other embodiments, the kit further contains a pair of primers for amplifying the promoter sequence of a reference gene.

In still other embodiments, the kit further contains a detectable probe, where the probe is capable of binding to the promoter sequence. In yet other embodiments, the probe is detected by fluorescence, by autoradiography, by an immunoassay, by an enzymatic assay, or by a colorimetric assay. In yet other embodiments, the kit further contains a reagent that converts methylated cytosine to uracil.

In yet another aspect, the invention provides a microarray containing at least two nucleic acid molecules, or fragments thereof, bound to a solid support, where the two nucleic acid molecules are selected from the group consisting of p16, ARF, GSTP1, MGMT, RAR-β2, TIMP3, CDH1, RASSF1A, and APC.

In yet another aspect, the invention provides a method for detecting a neoplasia in a biological sample. The method involves detecting the promoter methylation of at least two promoters in the sample by contacting the sample with a microarray of a previous aspect, where one of the promoters is selected from the group consisting of p16, ARF, GSTP1, MGMT, RAR-β2, TIMP3, CDH1, RASSF1A, and APC, and where an increased quantity of promoter methylation relative to a reference indicates the presence of a neoplasia in the sample.

In yet another aspect, the invention provides a collection of primers having a nucleic acid sequence selected from the group consisting of SEQ ID Nos.: 1-10 and 21-30.

In yet another aspect, the invention provides a probe having a nucleic acid sequence selected from the group consisting of SEQ ID Nos. 11-20.

In yet another aspect, the invention provides a collection of primer sets, each of the primer sets containing at least two primers that bind to a promoter selected from the group consisting of p16, ARF, GSTP1, MGMT, RAR-β2, TIMP3, CDH1, RASSF1A, and APC, the collection containing at least two primer sets.

In yet another aspect, the invention provides a method for identifying a subject having a renal neoplasia. The method involves determining the promoter methylation of at least one promoter in a biological sample from the subject, where an increase in promoter methylation in the sample relative to a reference identifies the subject as having a renal neoplasia.

In yet another aspect, the invention provides a method of diagnosing a subject as having a renal neoplasia. The method involves determining the promoter methylation of at least one promoter in a biological sample from the subject, where an increase in promoter methylation in the sample relative to a reference identifies the subject as having a renal neoplasia. In one embodiment, the subject is suspected of having a renal neoplasia.

In yet another aspect, the invention provides a method of monitoring a subject diagnosed as having a neoplasia. The method involves determining the methylation of a promoter, where an altered level (e.g., increased or decreased) of promoter methylation relative to the level of methylation in a reference indicates an altered severity of neoplasia in the subject. In one embodiment, the method is used to detect the recurrence of a renal neoplasia in a subject currently undergoing treatment or previously treated for renal neoplasia.

In yet another aspect, the invention provides a method of determining the stage of a renal neoplasia in a subject. The method involves determining the promoter methylation of at least one promoter in a biological sample from the subject, where an altered level (e.g., increased or decreased) of promoter methylation in the sample relative to a reference indicates an increased stage of neoplasia in the subject.

In yet another aspect, the invention provides a method of determining the clinical aggressiveness of a renal neoplasia in a subject. The method involves determining the promoter methylation of at least one promoter in a biological sample from the subject, where an altered level (e.g., increased or decreased) of promoter methylation in the sample relative to a reference level indicates an increased clinical aggressiveness of renal neoplasia.

In yet another aspect, the invention provides a method of selecting a treatment for a subject diagnosed as having a renal neoplasia. The method involves (a) determining the methylation of a promoter in a subject sample; and (b) selecting a treatment for the subject, where the treatment is selected from the group consisting of surgery, chemotherapy, and radiotherapy.

In yet another aspect, the invention provides a method of determining the prognosis of a subject diagnosed as having a renal neoplasia. The method involves determining the methylation of a promoter in a subject sample, where an altered level (e.g., increased or decreased) of promoter methylation relative to a reference indicates the prognosis of the subject the increase in the level of promoter methylation indicates a poor prognosis. In one embodiment, the increased level of promoter methylation indicates a poor prognosis. In another embodiment, the decreased level of promoter methylation indicates a good prognosis.

In yet another aspect, the invention provides a method for detecting renal neoplasia in a biological sample. The method involves determining the methylation of a promoter, where an increase in promoter methylation relative to a reference indicates the presence of renal cancer in the biological sample.

In yet another aspect, the invention provides a method for determining the methylation profile of a renal neoplasia. The method involves determining the methylation of a promoter selected from the group consisting of RASSF1A, TIMP3, CDH1, RAR-β2, p16, ARF, APC, GSTP1 and MGMT in a biologic sample, where the level of promoter methylation relative to a reference determines the methylation profile of the renal neoplasia.

In yet another aspect, the invention provides a kit for determining promoter methylation, the kit containing at least one nucleic acid molecule capable of binding selectively to a methylated or unmethylated promoter sequence selected from the group consisting of RASSF1A, TIMP3, CDH1, RAR-β2, p16, ARF, APC, GSTP1 and MGMT, and directions for using the nucleic acid molecule for the analysis of promoter methylation.

In yet another aspect, the invention provides a kit for determining promoter methylation, the kit containing at least one pair of primers capable of amplifying a promoter sequence selected from the group consisting of RASSF1A, TIMP3, CDH1, RAR-β2, p16, ARF, APC, GSTP1 and MGMT, where at least one of the primers binds selectively to a methylated or unmethylated sequence.

In various embodiments of the above aspects, the kit further contains directions for using the kit for the detection of a renal neoplasia. In other embodiments, the kit further contains a pair of primers for amplifying the promoter sequence of a reference gene; a detectable probe, where the probe is capable of binding to the promoter sequence; or a reagent that converts methylated cytosine to uracil. In other embodiments, the probe is detected by fluorescence, by autoradiography, by an immunoassay, by an enzymatic assay, or by a calorimetric assay.

In yet another aspect, the invention provides a microarray containing at least two nucleic acid molecules, or fragments thereof, bound to a solid support, where the two nucleic acid molecules are selected from the group consisting of RASSF1A, TIMP3, CDH1, RAR-β2, p16, ARF, APC, GSTP1 and MGMT.

In yet another aspect, the invention provides a method for detecting a neoplasia in a biologic sample. The method involves quantifying the promoter methylation of at least two promoters in the sample by contacting the sample with a microarray of a previous aspect, where one of the promoters is selected from the group consisting of RASSF1A, TIMP3, CDH1, RAR-β2, p16, ARF, APC, GSTP1 and MGMT, and where an increased quantity of promoter methylation relative to a reference indicates the presence of a neoplasia in the sample.

In yet another aspect, the invention provides a collection of primer sets, each of the primer sets containing at least two primers that bind to a promoter selected from the group consisting of RASSF1A, TIMP3, CDH1, RAR-β2, p16, ARF, APC, GSTP1 and MGMT, the collection containing at least two primer sets.

In yet another aspect, the invention provides a method for identifying a subject having a prostate neoplasia. The method involves determining the promoter methylation at a group of promoters containing Tazarotene-induced gene 1 (TIG1), adenomatous polyposis coli (APC), retinoic acid receptor β2 (RARβ2), and glutathione S-transferaseπ—(GSTP1) in a biological sample from the subject, where an increase in promoter methylation in the sample relative to a reference identifies the subject as having a prostate neoplasia.

In yet another aspect, the invention provides a method of diagnosing a subject as having a prostate neoplasia. The method involves determining the promoter methylation at a group of promoters containing TIG1, APC, RARβ2, and GSTP1 in a biological sample from the subject, where an increase in promoter methylation in the sample relative to a reference identifies the subject as having a prostate neoplasia. In one embodiment, the subject is suspected of having a prostate neoplasia.

In yet another aspect, the invention provides a method of monitoring a subject diagnosed as having a neoplasia. The method involves determining the promoter methylation at a group of promoters containing TIG1, APC, RARβ2, and GSTP1, where an altered level of promoter methylation relative to the level of methylation in a reference indicates an altered severity of neoplasia in the subject. In one embodiment, the method is used to detect the recurrence of a prostate neoplasia in a subject currently undergoing treatment or previously treated for prostate neoplasia.

In yet another aspect, the invention provides a method of determining the stage of a prostate neoplasia in a subject. The method involves determining the promoter methylation at a group of promoters containing TIG1, APC, RARβ2, and GSTP1 in a biological sample from the subject, where an increased level of promoter methylation in the sample relative to a reference indicates an increased stage of neoplasia in the subject.

In yet another aspect, the invention provides a method of determining the clinical aggressiveness of a prostate neoplasia in a subject. The method involves determining the promoter methylation at a group of promoters containing TIG1, APC, RARβ2, and GSTP1 in a biological sample from the subject, where an increased level of promoter methylation in the sample relative to a reference level indicates an increased clinical aggressiveness of prostate neoplasia.

In yet another aspect, the invention provides a method of selecting a treatment for a subject diagnosed as having a prostate neoplasia. The method involves (a) determining the promoter methylation at a group of promoters containing TIG1, APC, RARβ2, and GSTP1 in a subject sample; and (b) selecting a treatment for the subject, where the treatment is selected from the group consisting of surgery, chemotherapy, and radiotherapy.

In yet another aspect, the invention provides a method of determining the prognosis of a subject diagnosed as having a prostate neoplasia. The method involves determining the promoter methylation at a group of promoters containing TIG1, APC, RARβ2, and GSTP1, where an altered level of promoter methylation relative to a reference indicates the prognosis of the subject.

In yet another aspect, the invention provides a method for detecting a prostate neoplasia in a biological sample. The method involves determining the promoter methylation at a group of promoters containing TIG1, APC, RARβ2, and GSTP1, where an increase in promoter methylation relative to a reference indicates the presence of prostate cancer in the biological sample.

In yet another aspect, the invention provides a method for determining the methylation profile of a prostate neoplasia. The method involves determining the promoter methylation of a group of promoters containing TIG1, APC, RARβ2, and GSTP1 in a biologic sample, where the level of promoter methylation relative to a reference determines the methylation profile of the prostate neoplasia.

In yet another aspect, the invention provides a kit for determining promoter methylation, the kit containing at least one nucleic acid molecule capable of binding selectively to a methylated or unmethylated promoter sequence the method containing determining the promoter methylation at a group of promoters consisting of TIG1, APC, RARβ2, and GSTP1, and directions for using the nucleic acid molecule for the analysis of promoter methylation.

In yet another aspect, the invention provides a kit for determining promoter methylation, the kit containing at least one pair of primers capable of amplifying a promoter sequence selected from the group consisting of TIG1, APC, RARβ2, and GSTP1, where at least one of the primers binds selectively to a methylated or unmethylated sequence.

In various embodiments of the previous aspects, the kit further contains a pair of primers for amplifying the promoter sequence of a reference gene. In yet other embodiments, the kit further contains primers that amplify the promoter sequence of p16InK4a, p14/ARF, MGMT, CDH1, TIMP3, and Rassf1A. In still other embodiments, the kit further contains a detectable probe, where the probe is capable of binding to the promoter sequence. In yet other embodiments, the probe is detected by fluorescence, by autoradiography, by an immunoassay, by an enzymatic assay, or by a colorimetric assay. In yet other embodiments, the further contains a reagent that converts methylated cytosine to uracil.

In yet another aspect, the invention provides a microarray containing at least two nucleic acid molecules, or fragments thereof, bound to a solid support, where the two nucleic acid molecules are selected from the group consisting of TIG1, APC, RARβ2, and GSTP1. In one embodiment, the microarray further contains nucleic acid molecules or fragments thereof; selected from the group consisting of p16InK4a, p14/ARF, MGMT, CDH1, TIMP3, and Rassf1A.

In yet another aspect, the invention provides a method for detecting a neoplasia in a biologic sample. The method involves quantifying the promoter methylation of at least two promoters in the sample by contacting the sample with a microarray of a previous aspect, where one of the promoters is selected from the group consisting of TIG1, APC, RARβ2, and GSTP1, and where an increased quantity of promoter methylation relative to a reference indicates the presence of a neoplasia in the sample. In one embodiment, the method further involves determining the methylation of a promoter selected from the group consisting of p16InK4a, p14/ARF, MGMT, CDH1, TIMP3, and Rassf1A.

In yet another aspect, the invention provides a nucleic acid molecule that binds a TIG1 promoter, the primer having a nucleic acid sequence containing:

```
                              (SEQ ID NO: 31)
5'-TTTTTCGTCGCGGTTTGG-3'
or
                              (SEQ ID NO: 32)
5'-CGCTACCCGAACTTAATACTAAAATACG-3'.
```

In a related aspect, the invention provides a probe having a nucleic acid sequence containing 6-carboxyfluorescein-TCGGTTTTGCGTTGCGGAGGC-TAMRA (SEQ ID NO: 33).

In yet another aspect, the invention provides a collection of primer sets, each of the primer sets containing at least two primers that bind to a promoter selected from the group consisting of TIG1, APC, RARβ2, and GSTP1, the collection containing at least two primer sets. In one embodiment, the collection contains primer sets that bind a promoter selected from the group consisting of p16Ink4a, p14/ARF, MGMT, CDH1, TIMP3, and Rassf1A.

In various embodiments of any of the above aspects, the promoter is any one or more (e.g., two, three, four, five, six, seven, eight, nine, ten, or eleven) of p16, ARF, GSTP1, MGMT, RAR-β2, TIMP3, CDH1, RASSF1A, APC, LOXL1, or LOXL4 and the promoter methylation is determined at two, three, or four, five, six, seven, eight, or nine promoters. In other embodiments of any of the above aspects, the promoter methylation is determined for a group of promoters including p16, ARF, GSTP1, MGMT, RAR-β2, TIMP3, CDH1, RASSF1A, LOXL1, LOXL4, and/or APC. In yet other embodiments of the above aspects, the promoter methylation at a selected promoter (e.g., a promoter is selected from any one or more of p16, ARF, GSTP1, MGMT, RAR-β2, TIMP3, CDH1, RASSF1A, LOXL1, LOXL4, and APC) is compared to a reference (e.g., the level of methylation present in a sample previously obtained from the subject; a baseline level of methylation present in a sample from the subject obtained prior to therapy; or the level of methylation present in a normal subject sample. In still other embodiments of the above aspects, the level of methylation at a promoter (e.g., ARF and MGMT methylation) is indicative of tumor stage, correlate with increasing tumor (T) stage. In still other embodiments, an altered level of promoter methylation is an increase or decrease in promoter methylation. In still other embodiments, the increase in promoter methylation indicates that more aggressive therapy is appropriate. In still other embodiments, the altered level is an increase or a decrease in the level of promoter methylation relative to a reference. In various embodiments of the above aspects, the increase in p16, ARF, MGMT, and GSTP1 promoters is determined. In still other embodiments, the level of promoter methylation at an increased number of promoters increases specificity or increases sensitivity. In still other embodiments of any of the above aspects, the biological sample is a tissue sample, a biological sample that contains genetic material, such as any one or more of serum, plasma, ejaculate, urine or stool.

In still other embodiments of any of the above aspects, the promoter methylation is quantified by quantitative methylation-specific PCR (QMSP). In still other embodiments of any of the above aspects, the level or frequency of promoter methylation is quantified. In still other embodiments of any of the above aspects, the promoter is any one or more of RASSF1A, TIMP3, CDH1, RAR-β2, p16, ARF, APC, GSTP1, TIG1, LOXL1, LOXL4, and MGMT; or a group containing or consisting of RASSF1A, TIMP3, CDH1, RAR-β2, p16, ARF, APC, GSTP1, LOXL1, LOXL4 and MGMT. In still other embodiments of any of the above aspects, the promoter is any one or more of RASSF1A, TIMP3, CDH1, RAR-β2, p16, ARF, and APC. In still other embodiments of any of the above aspects, the promoter is any one or more of p16InK4a, p14/ARF, MGMT, CDH1, TIMP3, and Rassf1A. In still other embodiments the group contains or consists of p16, ARF, GSTP1, MGMT, RAR-β2, TIMP3, CDH1, RASSF1A, and APC; p16, ARF, MGMT, and GSTP1; p16InK4a, p14/ARF, MGMT, CDH1, TIMP3, and Rassf1A; p16, ARF, MGMT, and GSTP1 promoters; TIG1, APC, RARβ2, and GSTP1 promoters.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "alteration" is meant an increase or decrease. An alteration may be by as little as 1%, 2%, 3%, 4%, 5%, 10%, 20%, 30%, or by 40%, 50%, 60%, or even by as much as 75%, 80%, 90%, or 100%.

By "aggressive therapy" is meant any therapy having increased toxicity or other adverse effects relative to a conventional therapy. For example, a more aggressive therapy would include a higher dose of a chemotherapeutic relative to the dose typically given for treatment of a similar neoplastic condition.

By "biologic sample" is meant any tissue, cell, fluid, or other material derived from an organism.

By "clinical aggressiveness" is meant the severity of the neoplasia. Aggressive neoplasias are more likely to metastasize than less aggressive neoplasias. While conservative methods of treatment are appropriate for less aggressive neoplasias, more aggressive neoplasias require more aggressive therapeutic regimens.

By "control" is meant a standard of comparison. For example, the methylation level present at a promoter in a neoplasia may be compared to the level of methylation present at that promoter in a corresponding normal tissue.

By "diagnostic" is meant any method that identifies the presence of a pathologic condition or characterizes the nature of a pathologic condition. Diagnostic methods differ in their sensitivity and specificity. While a particular diagnostic method may not provide a definitive diagnosis of a condition, it suffices if the method provides a positive indication that aids in diagnosis.

By "frequency of methylation" is meant the number of times a specific promoter is methylated in a number of samples.

By "increased quantity of methylation" is meant a detectable positive change in the level, frequency, or amount of methylation. Such an increase may be by 5%, 10%, 20%, 30%, or by as much as 40%, 50%, 60%, or even by as much as 75%, 80%, 90%, or 100%.

By "methylation level" is meant the number of methylated alleles. Methylation level can be represented as the methylation present at a target gene/reference gene×1000. While the examples provided below describe specific cutoff values in the methylation ratio to distinguish neoplastic tissue from normal tissue, such cutoff values are merely exemplary. Any ratio that allows the skilled artisan to distinguish neoplastic tissue from normal tissue is useful in the methods of the invention. In various embodiments, the methylation ratio cut-off value is 1, 2, 3, 4, 5, 6, 7, 8, 9, or 10. One skilled in the art appreciates that the cutoff value is selected to optimize both the sensitivity and the specificity of the assay.

By "methylation profile" is meant the methylation level at two or more promoters.

By "reference" is meant a control value used for comparison. Standard control values are typically those found in corresponding biological samples obtained from healthy subjects.

By "sensitivity" is meant the percentage of subjects with a particular disease that are correctly detected as having the disease. For example, an assay that detects 98/100 prostate carcinomas has 98% sensitivity.

By "severity of neoplasia" is meant the degree of pathology. The severity of a neoplasia increases, for example, as the stage or grade of the neoplasia increases.

By "specificity" is meant the percentage of subjects without a particular disease who test negative.

By "neoplasia" is meant a disease that is caused by or results in inappropriately high levels of cell division, inappropriately low levels of apoptosis, or both. For example, cancer is an example of a neoplasia.

By "periodic" is meant at regular intervals. Periodic patient monitoring includes, for example, a schedule of tests that are administered daily, bi-weekly, bimonthly, monthly, bi-annually, or annually.

By "promoter" is meant a nucleic acid sequence sufficient to direct transcription. In general, a promoter includes, at least, 50, 75, 100, 125, 150, 175, 200, 250, 300, 400, 500, 750, 1000, 1500, or 2000 nucleotides upstream of a given coding-sequence (e.g., upstream of the coding sequence for GSTP1, MGMT, p14/ARF, p16/INK4a, RASSFIA, APC, TIMP3, Tazarotene-induced gene 1 (TIG1), E-cadherin (CDH1), and RARβ2). Exemplary promoter sequences for each of the following genes is provided at the corresponding GenBank Accession No: APC (U02509); ARF (AF082338); CDH1 (L34545); GSTP1 (M24485); MGMT (X61657); P16 (U12818), RARβ2 (X56849) Rassf1A (NM 007182); TIMP3 (U33110), Tazarotene-induced gene 1 (TIG1) is NT_005612, LOXL1 is NM_005576 (gi:5031882), or LOXL4 is NM_032211 (gi: 19923658).

By "tumor invasiveness" is meant the tumor's propensity to metastasize.

Other features and advantages of the invention will be apparent from the detailed description, and from the claims

BRIEF DESCRIPTION OF THE DRAWINGS

FIG. 1 shows a summary of aberrant promoter methylation in primary tumor and urine sediment samples of bladder cancer patients. T and U denote tumor and urine respectively. In general, the identical methylation pattern was found in urine sediment. There were no cases where methylation was positive in urine but not in tumor.

FIGS. 8A-8I are dot plots showing the methylation levels of TIMP3, RARβ2, ARF, RASSF1A, APC, CDH1, GSTP1, p16, and MGMT in renal cancer tissue (T), urine (U), and serum (S) samples from renal cancer patients and 91 urine (UC) and 30 serum (SC) samples from control individuals without genitourinary cancer. Calculation of the target gene: β-actin ratios were based on the fluorescence emission intensity values for the gene of interest and β-actin obtained by quantitative real-time PCR analysis. The relative amount of methylated promoter DNA is much higher in matched urine sediment and serum DNA samples from cancer patients than in the few control urine and serum samples with methylation. Black bar represent the cutoff value for each gene. Values designated as 0.001 are zero values, which cannot be plotted correctly on a log scale.

FIG. 9 shows representative results of quantitative real-time methylation-specific PCR amplification plots for TIG1. The quantitative real-time methylation-specific PCR results of prostate cancer cell line PC3 as a positive control (A), sextant biopsy samples from prostate cancer patient (sample 61514; B, left mid biopsy in cancer region; C, right mid biopsy in nontumor region) and normal prostate tissue from a cystoprostatectomy case for bladder carcinoma (sample 11600, left apex biopsy; D). All samples were run in triplicate. The X axis indicates PCR cycle numbers, and the Y axis indicates ΔRn, which is defined as the cycle-to-cycle change in the reporter fluorescence signal normalized to a passive reference signal. Cancer sample "B" showed TIG1 methylation, whereas another sample "C" was unmethylated. Sample "D" from normal prostate tissue did not show amplification indicating absence of methylation.

DETAILED DESCRIPTION OF THE INVENTION

Figure 2:
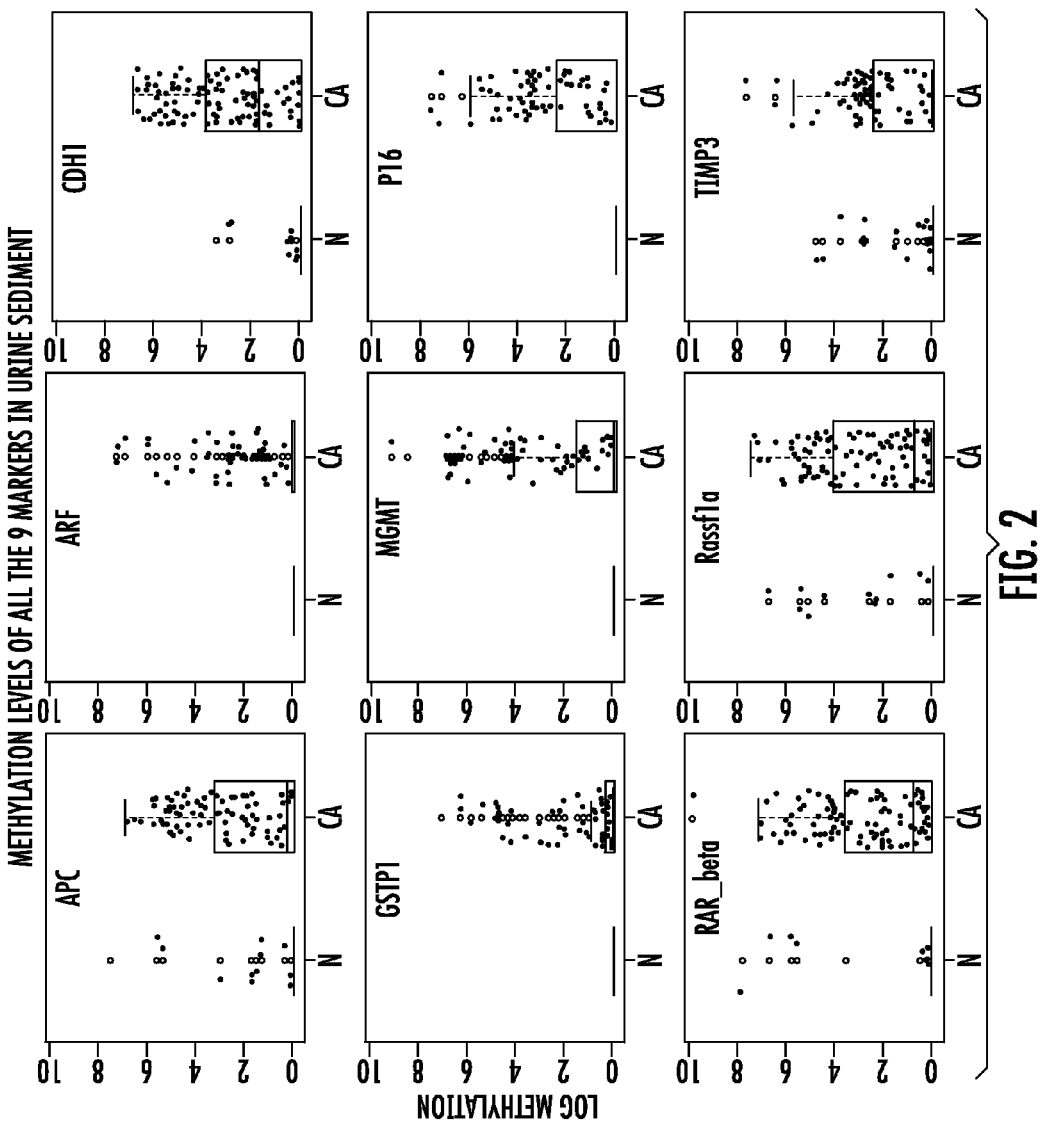
FIG. 2 shows nine dot plots that display methylation levels of nine marker genes in urine sediment of bladder cancer patients (Cases) (CA) and urine from age-matched controls (N). Calculation of the gene of interest: β-actin ratios were based on the fluorescence emission intensity values for both the gene of interest and β-actin obtained by quantitative real-time PCR analysis. The relative amount of methylated promoter DNA is much higher in urine sediment of bladder cancer patients than normal controls. This is seen most clearly in the boxplots, which show the inner 50% of the data, almost all of which is contained in the zero categories of the normal patients, with the boxes extending up in the cancer patients.

As described in more detail below, the present invention generally features composition and methods useful for the identification, monitoring, or diagnosis of subjects having a bladder, renal, or prostate neoplasia. In particular, the invention provides methods of screening a biological sample obtained from a subject to identify alterations in promoter methylation that are useful in identifying patients having a bladder, renal, or prostate neoplasia. Because the biological samples are obtained non-invasively, the methods are suitable for patient screening, diagnosis, prognosis, or for monitoring the treatment or post-surgical care of a patient diagnosed as having a bladder, renal, or prostate neoplasia.

Promoter Hypermethylation in Neoplasia

Aberrant promoter hypermethylation is a major mechanism for silencing tumor suppressor or other cancer-associated genes in many kinds of human cancer (Bird et al. Nat Med 1995; 1:686-92; Baylin et al., Adv Cancer Res 1998; 72:141-96; Esteller et al., Oncogene 1998; 17:2413-7; Herman et al., Proc Natl Acad Sci USA 1998; 95:6870-5). Genes such as APC, CDH1, RARβ2 and RASSF1A have been found to harbor hypermethylated promoters in over 35% of bladder tumors (Maruyama Cancer Res 2001; 61:8659-63; Chan et al., Clin Cancer Res 2002; 8:464-70). The development of real-time methylation specific PCR has simplified the study of genes inactivated by promoter hypermethylation in human cancer and has the advantage of increasing specificity due to the use of an internally binding fluorogenic hybridization probe for each gene.

Bladder Carcinoma

Endoscopic evaluation of the bladder with biopsy of suspicious lesions remains the standard method of bladder cancer diagnosis. Recent efficacy studies of cystoscopy and biopsy indicate that tumors are "missed" in 10-40% of patients. The present invention features highly reliable, noninvasive tools for bladder cancer diagnosis that provide for earlier and more accurate detection of bladder carcinomas. Such methods will likely improve the prognosis of patients with bladder cancer. At present, even after complete transurethral resection (TUR) of the tumor, 50% to 70% of superficial bladder tumors recur and 10-20% progress in stage and grade (Rubben et al., J Urol 1988; 139:283-5). Definitive noninvasive screening, diagnosis and patient monitoring following surgery would likely improve the management of bladder tumors and provide for the more effective treatment of patients with invasive disease. The invention provides methods for determining the quantitative methylation of a panel of genes that can be used for bladder cancer screening, diagnosis, prognosis, and patient monitoring.

Renal Carcinoma

Current methods for diagnosing renal carcinoma also rely on cytological analysis. The present invention provides for the detection of aberrant methylation in urine sediment or serum DNA. Such methods are useful for the noninvasive diagnosis of renal cancer. Apart from early detection, the detection of aberrant methylation in the urine or serum DNA of a patient may be used to monitor disease progress after curative surgery. When methylated DNA disappears in urine or serum shortly after curative surgery, the subsequent reappearance of these markers in a patient sample indicates a recurrence of disease. Such recurrence identifies the patient as requiring more intensive screening and aggressive treatment. The detection of aberrant methylation in urine or serum can also be used as a tool for the early detection and surveillance of renal cancer. Furthermore, the panel of genes identified herein could be expanded to simultaneously provide molecular staging and prognostic information in addition to detection.

Prostate Carcinoma

The invention also features methods for monitoring the methylation of genes that can be used in prostate cancer screening, diagnosis, prognosis, and patient monitoring. Such methods have increased sensitivity for prostate carcinoma detection relative to conventional methods of diagnosis, which typically rely on the histological review of frozen sections. The use of a panel of methylation markers as an adjunct or replacement for histologic review may substantially augment prostate cancer diagnosis from needle biopsies.

Types of Biological Samples

The level of promoter methylation in each of the genes identified herein can be measured in different types of biologic samples. Advantageously, the invention provides methods for detecting the presence of a neoplasia using a biological sample that is obtained by non-invasive means. Such biological samples include biologic fluids. Biological fluid samples, such as plasma, urine, seminal fluids, ejaculate, blood, blood serum, or any other biological fluid are useful in the methods of the invention. Stool samples are another biological sample that can be obtained via non-invasive means and that is useful in the methods described herein. Alternatively, the biologic sample is a tissue sample that includes cells of a tissue or organ (e.g., bladder tissue cells, prostatic tissue cells, renal tissue cells) or cellular materials, such as DNA. Such tissues are obtained, for example, from a biopsy.

Diagnostic Assays

The present invention provides a number of diagnostic assays that are useful for the identification or characterization of a neoplasia (e.g., bladder, renal, or prostate cancer). In one embodiment, a neoplasia is characterized by quantifying or determining the methylation level of one or more of the following promoters: pi-class glutathione S-transferase (GSTP1), 06-methylguanine DNA methyltransferase (MGMT), p14/ARF, (ARF) p16/INK4a (p16), RAS-associated domain family 1A (RASSFIA), adenomatous polyposis coli (APC), tissue inhibitor of metalloproteinase-3 (TIMP3), cellular retinoid binding protein 1 (CRBP1), or retinoic acid receptor β2 (RARβ2), E-cadherin (CDH1), Tazarotene-induced gene 1 (TIG1), LOXL1 or LOXL4 in the neoplasia. In one embodiment, methylation levels are determined using quantitative methylation specific PCR (QMSP) to detect CpG methylation in genomic DNA. QMSP uses sodium bisulfate to convert unmethylated cytosine to uracil. A comparison of sodium bisulfate treated and untreated DNA provides for the detection of methylated cytosines.

While the examples provided below describe methods of detecting methylation levels using QMSP, the skilled artisan appreciates that the invention is not limited to such methods. Methylation levels are quantifiable by any standard method, such methods include, but are not limited to real-time PCR, Southern blot, bisulfite genomic DNA sequencing, restriction enzyme-PCR, MSP (methylation-specific PCR), methylation-sensitive single nucleotide primer extension (MS-SNuPE) (see, for example, Kuppuswamy et al., *Proc. Natl Acad. Sci. USA*, 88, 1143-1147, 1991), DNA microarray based on fluorescence or isotope labeling (see, for example, Adorján Nucleic Acids Res., 30: e21 and Hou Clin. Biochem., 36:197-202, 2003), mass spectroscopy, methyl accepting capacity assays, and methylation specific antibody binding. See also U.S. Pat. Nos. 5,786,146, 6,017,704, 6,300,756, and 6,265,171.

The primers used in the invention for amplification of the CpG-containing nucleic acid in the specimen, after bisulfite modification, specifically distinguish between untreated or unmodified DNA, methylated, and non-methylated DNA. Methylation specific primers for the non-methylated DNA preferably have a T in the 3' CG pair to distinguish it from the C retained in methylated DNA, and the compliment is designed for the antisense primer. Methylation specific primers usually contain relatively few Cs or Gs in the sequence since the Cs will be absent in the sense primer and the Gs absent in the antisense primer (C becomes modified to U(uracil) which is amplified as T(thymidine) in the amplification product).

The primers of the invention embrace oligonucleotides of sufficient length and appropriate sequence so as to provide specific initiation of polymerization on a significant number of nucleic acids in the polymorphic locus. Specifically, the term "primer" as used herein refers to a sequence comprising two or more deoxyribonucleotides or ribonucleotides, preferably more than three, and most preferably more than 8, which sequence is capable of initiating synthesis of a primer extension product, which is substantially complementary to a polymorphic locus strand. The primer must be sufficiently long to prime the synthesis of extension products in the presence of the inducing agent for polymerization. The exact length of primer will depend on many factors, including temperature, buffer, and nucleotide composition. The oligonucleotide primer typically contains between 12 and 27 or more nucleotides, although it may contain fewer nucleotides. Primers of the invention are designed to be "substantially" complementary to each strand of the genomic locus to be amplified and include the appropriate G or C nucleotides as discussed above. This means that the primers must be sufficiently complementary to hybridize with their respective strands under conditions that allow the agent for polymerization to perform. In other words, the primers should have sufficient complementarity with the 5' and 3' flanking sequences to hybridize therewith and permit amplification of the genomic locus. While exemplary primers are provided herein, it is understood that any primer that hybridizes with the target sequences of the invention are useful in the method of the invention for detecting methylated nucleic acid.

In one embodiment, methylation specific primers amplify a desired genomic target using the polymerase chain reaction (PCR). The amplified product is then detected using standard methods known in the art. In one embodiment, a PCR product (i.e., amplicon) or real-time PCR product is detected by probe binding. In one embodiment, probe binding generates a fluorescent signal, for example, by coupling a fluorogenic dye molecule and a quencher moiety to the same or different oligonucleotide substrates (e.g., TaqMan® (Applied Biosystems, Foster City, Calif., USA), Molecular Beacons (see, for example, Tyagi et al., Nature Biotechnology 14(3):303-8, 1996), Scorpions® (Molecular Probes Inc., Eugene, Oreg., USA)). In another example, a PCR product is detected by the binding of a fluorogenic dye that emits a fluorescent signal upon binding (e.g., SYBR® Green (Molecular Probes)). Such detection methods are useful for the detection of a methylation specific PCR product.

The methylation level of any two or more of the promoters described herein defines the methylation profile of a neoplasia. The level of methylation present at any particular promoter is compared to a reference. In one embodiment, the reference is the level of methylation present in a control sample obtained from a patient that does not have a neoplasia. In another embodiment, the reference is a baseline level of methylation present in a biologic sample derived from a patient prior to, during, or after treatment for a neoplasia. In yet another embodiment, the reference is a standardized curve.

The methylation level of any one, two, three, four, five, six, seven, eight, nine, ten, eleven or more promoters (e.g., pi-class glutathione S-transferase (GSTP1), O6-methylguanine DNA methyltransferase (MGMT), p14/ARF, (ARF) p16/INK4a (p16), RAS-associated domain family 1A (RASS-FIA), adenomatous polyposis coli (APC), tissue inhibitor of metalloproteinase-3 (TIMP3), cellular retinoid binding protein 1 (CRBP1), or retinoic acid receptor β2 (RARβ2), E-cadherin (CDH1), Tazarotene-induced gene 1 (TIG1)), LOXL1 or LOXL4 is used, alone or in combination with other standard methods, to determine the stage or grade of a neoplasia. Grading is used to describe how abnormal or aggressive the neoplastic cells appear, while staging is used to describe the extent of the neoplasia. The grade and stage of the neoplasia is indicative of the patient's long-term prognosis (i.e., probable response to treatment and survival). Thus, the methods of the invention are useful for predicting a patient's prognosis, and for selecting a course of treatment.

Cancer Prognosis

The most method for staging cancer is known as the 'tumour, node, metastasis' (TNM) system. This staging system takes into account the size of the tumour, whether there is cancer in the lymph nodes and whether the cancer has spread to any other part of the body.

Bladder Cancer

Bladder cancers usually arise from the transitional cells of the bladder (the cells lining the bladder). These tumors may be classified based on their growth pattern as either papillary tumors (meaning they have a wart-like lesion attached to a stalk) or nonpapillary tumors. Nonpapillary tumors are much less common, but they are more invasive and have a poorer prognosis. Bladder cancer is typically staged as follows:

TX: Primary tumor cannot be assessed
T0: No evidence of primary tumor
Ta: Noninvasive papillary carcinoma
Tis: Carcinoma in situ (i.e., flat tumor)
T1: Tumor invades subepithelial connective tissue
T2: Tumor invades muscle
pT2a: Tumor invades superficial muscle (inner half)
pT2b: Tumor invades deep muscle (outer half)
T3: Tumor invades perivesical tissue
pT3a: Microscopically
pT3b: Macroscopically (extravesical mass)
T4: Tumor invades any of the following: prostate, uterus, vagina, pelvic wall, or abdominal wall
T4a: Tumor invades the prostate, uterus, vagina
T4b: Tumor invades the pelvic wall, abdominal wall Bladder cancer spreads by extending into the nearby organs, including the prostate, uterus, vagina, ureters, and rectum. It can also spread to the pelvic lymph nodes or to other parts of the body, such as the liver, lungs and bones.

Renal Carcinoma

Renal cell carcinoma is the most common form of kidney cancer in adults.

Kidney cancer is typically staged as follows:
Stage I is an early stage of kidney cancer. The tumor measures up to 2¾ inches (7 centimeters). Cancer cells are found only in the kidney.
Stage II is also an early stage of kidney cancer, but the tumor measures more than 2¾ inches. The cancer cells are found only in the kidney.
Stage III is one of the following:
The tumor does not extend beyond the kidney, but cancer cells have spread through the lymphatic system to one nearby lymph node; or
The tumor has invaded the adrenal gland or the layers of fat and fibrous tissue that surround the kidney, but cancer cells have not spread beyond the fibrous tissue. Cancer cells may be found in one nearby lymph node; or
The cancer cells have spread from the kidney to a nearby large blood vessel. Cancer cells may be found in one nearby lymph node.
Stage IV is one of the following:
The tumor extends beyond the fibrous tissue that surrounds the kidney; or
Cancer cells are found in more than one nearby lymph node; or
The cancer has spread to other places in the body such as the lungs.

Renal cancer metastasizes aggressively, most often to the lungs and other organs. About one-third of patients have metastasis at the time of diagnosis. Given the risk of metastasis, renal carcinomas are typically treated aggressively.

Prostate Cancer

The Gleason scale is the most common scale used for grading prostate cancer. A pathologist will look at the two most poorly differentiated parts of the tumor and grade them. The Gleason score is the sum of the two grades, and so can range from two to 10. The higher the score is, the poorer the prognosis. Scores usually range between 4 and 7. The scores can be broken down into three general categories: (i) low-grade neoplasias (score<4) are typically slow-growing and contain cells that are most similar to normal prostate cells; intermediate grade neoplasias (4<score<7) are the most common and typically contain some cells that are similar to normal prostate cells as well as some more abnormal cells; high-grade neoplasias (8<score<10) contain cells that are most dissimilar to normal prostate cells. High-grade neoplasias are the most deadly because they are most aggressive and fast growing. High-grade neoplasias typically move rapidly into surrounding tissues, such as lymph nodes and bones.

Stage refers to the extent of a cancer. In prostate cancer, for example, one staging method divides the cancer into four categories, A, B, C, and D. Stage A describes a cancer that is only found by elevated PSA and biopsy, or at surgery for obstruction. It is not palpable on digital rectal exam (DRE). This stage is localized to the prostate. This type of cancer is usually curable, especially if it has a relatively low Gleason grade. Stage B refers to a cancer that can be felt on rectal examination and is limited to the prostate. Bone scans or CT/MRI scans are often used to determine this stage, particularly if prostate specific antigen (PSA) levels are significantly elevated or if the Gleason grade is 7 or greater. Many Stage B prostate cancers are curable. Stage C cancers have spread beyond the capsule of the prostate into local organs or tissues, but have not yet metastasized to other sites. This stage is determined by DRE, or CT/MRI scans, and/or sonography. In Stage C a bone scan or a PROSTASCINT scan is negative. Some Stage C cancers are curable. Stage D cancer has metastasized to distant lymph nodes, bones or other sites. This is usually determined by bone scan, PROSTASCINT scan, or other studies. Stage D cancer is usually incurable, but may be treatable.

Selection of a Treatment Method

After a subject is diagnosed as having a neoplasia (e.g., bladder, renal, prostate cancer) a method of treatment is selected. For bladder, renal, or prostate cancer a number of standard treatment regimens are available. The methylation profile of the neoplasia, or the level of methylation at a particular promoter, is used in selecting a treatment method. In one embodiment, less aggressive neoplasias have lower methylation levels than more aggressive neoplasias. In another embodiment, the methylation profile of a neoplasia, or the level of methylation at a particular promoter is correlated with a clinical outcome using statistical methods to determine the aggressiveness of the neoplasia. Methylation profiles that correlate with poor clinical outcomes, such as metastasis or death, are identified as aggressive neoplasias. Methylation profiles that correlate with good clinical outcomes are identified as less aggressive neoplasias.

Bladder Cancer

The choice of an appropriate treatment for bladder cancer is based on the stage of the tumor, the severity of the symptoms, and the presence of other medical conditions as determined using the methods of the invention, alone or in combination with other diagnostics. Generally, less aggressive tumors are treated by removing the tumor without removing the rest of the bladder. Chemotherapy may also be administered. Often chemotherapeutic agents are administered directly into the bladder often in conjunction with immunotherapy. More aggressive tumors or higher stage tumors are treated by removing the tumor and administering immunotherapy. For patients with the most aggressive or highest stage tumors, more aggressive therapies are required. Such therapy includes removing the bladder and administering a combination of chemotherapy and radiation therapy.

Renal Cancer

Renal cancer is typically treated by surgery, arterial embolization, radiation therapy, biological therapy, or chemotherapy, or some combination of these therapies. Methods of the invention are useful for choosing an appropriate treatment method. In general, renal cancer is treated by the removal of all or part of the kidney. Depending on the stage of the tumor and its aggressiveness removal of the bladder or surrounding tissues or lymph nodes may also be required. Hormone treatments may reduce the growth of the tumor in some cases. Medications, such as alpha-interferon and interleukin, are used to inhibit the growth of some renal cell carcinomas. In addition, angiogenesis inhibitors, such as Nexavar, may be used for the treatment of advanced renal cell carcinoma. Chemotherapy may also be used.

Prostate Cancer

Less aggressive prostate neoplasias are likely to be susceptible to conservative treatment methods. Conservative treatment methods include, for example, cancer surveillance, which involves periodic patient monitoring using diagnostic assays of the invention, alone or in combination, with PSA blood tests and DREs, or hormonal therapy. Cancer surveillance is selected when diagnostic assays indicate that the adverse effects of treatment (e.g., impotence, urinary, and bowel disorders) are likely to outweigh therapeutic benefits.

More aggressive bladder, renal, and prostate neoplasias are less susceptible to conservative treatment methods. When methods of the invention indicate that a neoplasia is very aggressive, an aggressive method of treatment should be selected. Aggressive therapeutic regimens typically include one or more of the following therapies: surgery, radiation therapy (e.g., external beam and brachytherapy), hormone therapy, and chemotherapy.

Patient Monitoring

The diagnostic methods of the invention are also useful for monitoring the course of a neoplasia in a patient or for assessing the efficacy of a therapeutic regimen. In one embodiment, the diagnostic methods of the invention are used periodically to monitor the methylation level of any one, two, three, four, five, six, seven, eight, nine, ten, eleven or more promoters (e.g., pi-class glutathione S-transferase (GSTP1), O6-methylguanine DNA methyltransferase (MGMT), p14/ARF, (ARF) p16/INK4a (p16), RAS-associated domain family 1A (RASSFIA), adenomatous polyposis coli (APC), tissue inhibitor of metalloproteinase-3 (TIMP3), cellular retinoid binding protein 1 (CRBP1), or retinoic acid receptor β2 (RARβ2), E-cadherin (CDH1), Tazarotene-induced gene 1 (TIG1) LOXL1 or LOXL4). In one example, the neoplasia is characterized using a diagnostic assay of the invention prior to administering therapy. This assay provides a baseline that describes the methylation level of one or more promoters or the methylation profile of the neoplasia prior to treatment. Additional diagnostic assays are administered during the course of therapy to monitor the efficacy of a selected therapeutic regimen. A therapy is identified as efficacious when a diagnostic assay of the invention detects a decrease in methylation levels at one or more promoters relative to the baseline level of methylation.

Microarray Procedure

The methods of the invention may also be used for microarray-based assays that provide for the high-throughput analysis of methylation at a large numbers of genes and CpG dinucleotides in parallel. Microarrays of the invention are useful to assay the methylation level of any one, two, three, four, five, six, seven, eight, nine, ten, eleven or more promoters (e.g., pi-class glutathione S-transferase (GSTP1), O6-methylguanine DNA methyltransferase (MGMT), p14/ARF, (ARF) p16/INK4a (p16), RAS-associated domain family 1A (RASSFIA), adenomatous polyposis coli (APC), tissue inhibitor of metalloproteinase-3 (TRMP3), cellular retinoid binding protein 1 (CRBP1), retinoic acid receptor β2 (RARβ2), E-cadherin (CDH1), Tazarotene-induced gene 1 (TIG1), LOXL1 or LOXL4). Such methods are known in the art, and are described, for example, in U.S. Pat. No. 6,214,556. (See also, Adorjan et al., Nucleic Acids Research, 30:e21, 2002). In brief, oligonucleotides with a C6-amino modification at the 5'-end are immobilized on a solid substrate at fixed positions to form an array. Useful substrate materials include membranes, composed of paper, nylon or other materials, filters, chips, glass slides, and other solid supports. The ordered arrangement of the array elements allows hybridization patterns and intensities to be interpreted as methylation levels of particular genes. For each analyzed CpG position two oligonucleotides, reflecting the methylated and non-methylated status of the CpG dinucleotides, are immobilized at specific loci on the array. Oligonucleotides may be designed to match only the bisulphite-modified DNA fragments; this excludes signals arising from incomplete bisulphite conversion. The oligonucleotide microarrays are hybridized with detectably labeled PCR products. Such PCR products are amplified from a biological sample using any method known in the art. Hybridization conditions are optimized to allow detection of the differences between the TG and CG variants. Exemplary hybridization conditions are described herein. Subsequently, images of the hybridized arrays are obtained using any desired detection method. The degree of methylation at any specific CpG position can then be quantified.

Kits

The invention also provides kits for the diagnosis or monitoring of a neoplasia in a biological sample obtained from a subject. In various embodiments, the kit includes at least one primer or probe whose binding distinguishes between a methylated and an unmethylated sequence, together with instructions for using the primer or probe to identify a neoplasia. In another embodiment, the kit further comprises a pair of primers suitable for use in a polymerase chain reaction (PCR). In yet another embodiment, the kit further comprises a detectable probe. In yet another embodiment, the kit further comprises a pair of primers capable of binding to and amplifying a reference sequence. In yet other embodiments, the kit comprises a sterile container which contains the primer or probe; such containers can be boxes, ampules, bottles, vials, tubes, bags, pouches, blister-packs, or other suitable container form known in the art. Such containers can be made of plastic, glass, laminated paper, metal foil, or other materials suitable for holding nucleic acids. The instructions will generally include information about the use of the primers or probes described herein and their use in diagnosing a neoplasia. Preferably, the kit further comprises any one or more of the reagents described in the diagnostic assays described herein. In other embodiments, the instructions include at least one of the following: description of the primer or probe; methods for using the enclosed materials for the diagnosis of a neoplasia; precautions; warnings; indications; clinical or research studies; and/or references. The instructions may be printed directly on the container (when present), or as a label applied to the container, or as a separate sheet, pamphlet, card, or folder supplied in or with the container.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

It should be appreciated that the invention should not be construed to be limited to the examples that are now described; rather, the invention should be construed to include any and all applications provided herein and all equivalent variations within the skill of the ordinary artisan.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with bladder, renal, or prostate cancer, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

EXAMPLES

Example 1

Bladder Carcinoma

The demographic and clinical characteristics of cancer patients included in this study are summarized in Table 1 (below).

TABLE 1

Demographic and clinical information of bladder cancer patients

| Histological Cell Type | |
|---|---|
| TCC | 157 |
| Adeno | 4 |
| Squamous | 2 |
| Mixed | 1 |
| Other | 2 |
| Large cell | 3 |
| Small cell | 2 |
| Carcinosarcoma | 4 |
| Race | |
| White | 126 |
| Hispanic | 1 |
| African American | 11 |
| Other | 6 |
| Unknown | 31 |
| Smoking | |
| Yes | 93 |
| No | 25 |
| Unknown | 57 |
| Sex | |
| Female | 47 |
| Male | 128 |
| Grade ‡ | |
| Lower grade (grade 1 and 2) | 30 |
| Higher grade (grade 3) | 137 |
| Unknown | 8 |
| Metastasis | |
| Yes | 39 |
| No | 128 |
| Unknown | 8 |
| Alcohol | |
| Drinker | 50 |
| Not drinker or rarely drinker | 51 |
| Unknown | 74 |
| Stage † | |
| pTa | 32 |
| PTis | 16 |
| pT1 | 26 |
| pT2a, pT2b | 31 |
| pT3a, pT3b | 54 |
| pT4 | 16 |
| Noninvasive (Ta-T1) | 74 |
| Muscle invasive (≥pT2) | 101 |
| Recurrence | |
| Yes | 29 |
| No | 128 |
| unknown | 18 |

† American Joint Committee on Cancer staging
‡ American Joint Committee on Cancer The study population was predominantly male (73%), with a median age of 67 years (interquartile range 29-90 years). Bladder cancer cases were identified by cystoscopy and/or cytology and all were eventually confirmed by standard pathology. Most of the tumors were transitional cell carcinomas of all stages and grades (Table 1).

Figure 1:
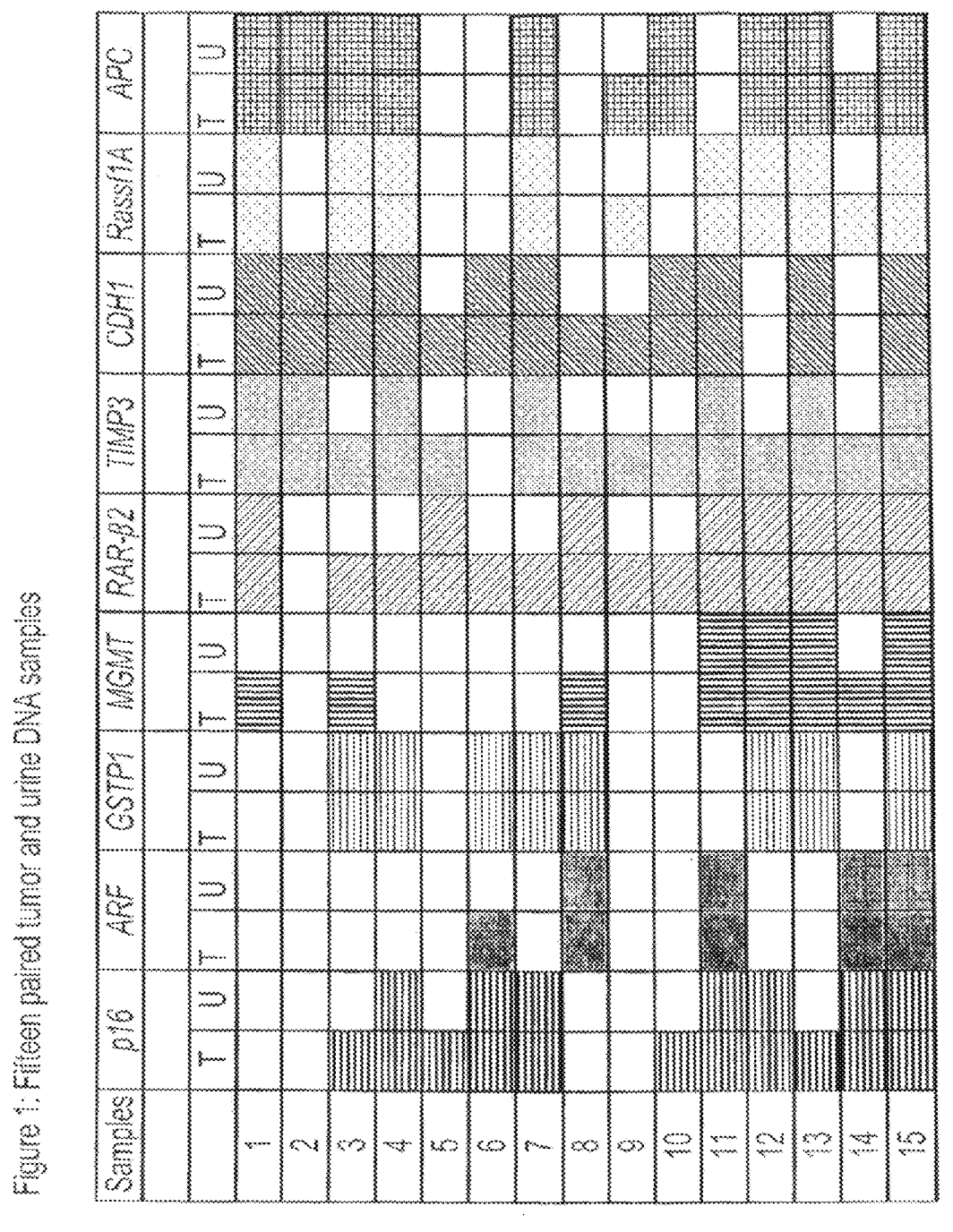

The promoter methylation pattern of APC, ARF, CDH1, GSTP1, MGMT, p16; RAR-β2, RASSF1A, and TIMP3 was determined in fifteen primary bladder tumors and corresponding matched urine DNAs. The methylation pattern of nine individual genes in primary tumor and matched urine DNA are shown in FIG. 1. Identical methylation profiles were found in the corresponding tumor; aberrant methylation was not detected in the urine of bladder cancer patients without methylation in the corresponding tumor. Generally, relative methylation values (number of methylated alleles) were higher in tumor than in urine sediments. Twenty-five initial urine controls were tested and the absence of methylation in four genes and low levels of methylation in five genes was observed.

The quantitative analysis was then extended from the initial fifteen cancer cases and twenty-five initial controls, to an additional 160 urine samples of bladder cancer patients and 69 controls (total 94). Control patients had no evidence of genitourinary malignancy. The frequency of methylation in primary tumor and the analytical sensitivity of the assay is summarized in Table 2.

TABLE 2

Sensitive detection of cancer in urine using DNA methylation markers

| Markers | Frequency of methylation in Primary tumors | Analytical sensitivity |
|---|---|---|
| P16 | 11/15(73%) | 7/11(63.63%) |
| ARF | 5/15(33%) | 4/5(80%) |
| GSTP1 | 7/15(47%) | 7/7(100%) |
| MGMT | 8/15(53%) | 4/8(50%) |
| RAR-β2 | 14/15(93%) | 9/14(64%) |
| TIMP3 | 14/15(93%) | 7/14(50%) |
| CDH1 | 13/15(87%) | 10/13(76.92%) |
| Rassf1A | 10/15(67%) | 8/10(80%) |
| APC | 11/15(73%) | 8/11(73%) |

Analytical sensitivity defined as the fraction of cases in which methylation of a marker is found in urine for cases with confirmed methylation of the same marker in the associated tumor In the primary tumor samples, the frequency of methylation in each locus ranged from 5/15 (33%) to 14/15 (93%). The analytical sensitivity of each individual gene ranged from 7/7 (100%) to 7/14 (50%) (Table 2). In the entire population aberrant promoter methylation was detected in urine in 45% (79 of 175) of samples for p16, 28% (49 of 175) for ARF, 35% (61 of 175) for MGMT, 43% (75 of 175) for GSTP1, and 62% (109 of 175) for Rassf1A. Distribution of relative methylation values (gene/β-actin X 1000) of QMSP in urine sediment DNA from cancer patients and normal controls is shown in FIG. 2 as dot plots.

Figure 3:
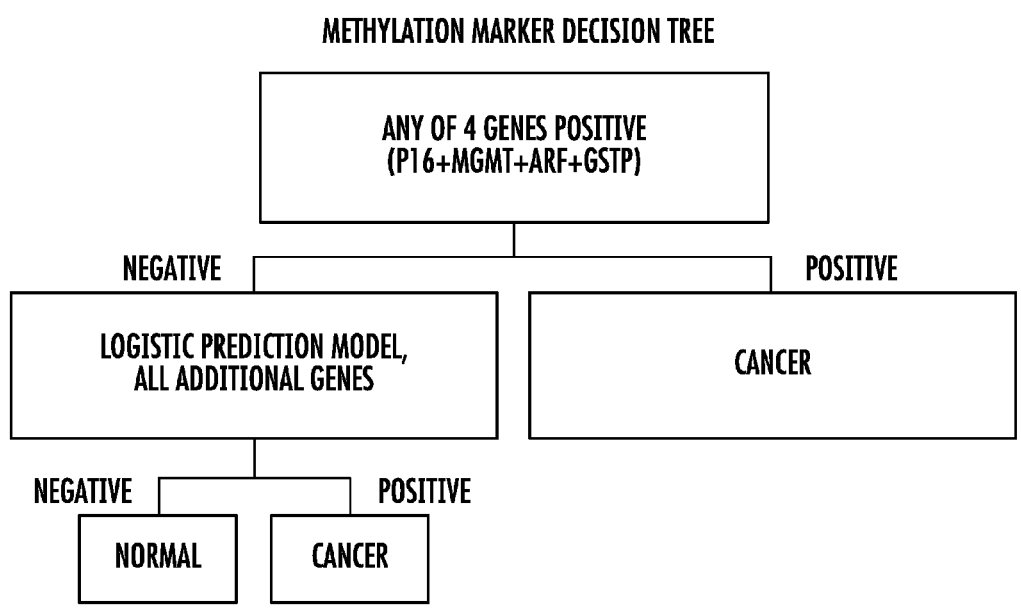
FIG. 3 shows a methylation marker decision tree. This illustrates a two-stage diagnostic algorithm wherein those who are positive on any of the 4 genes are classified as having cancer, and those who are negative on all 4 genes go to a second stage where additional marker gene promoter methylation is determined and their logistic risk score calculated.
Figure 4:
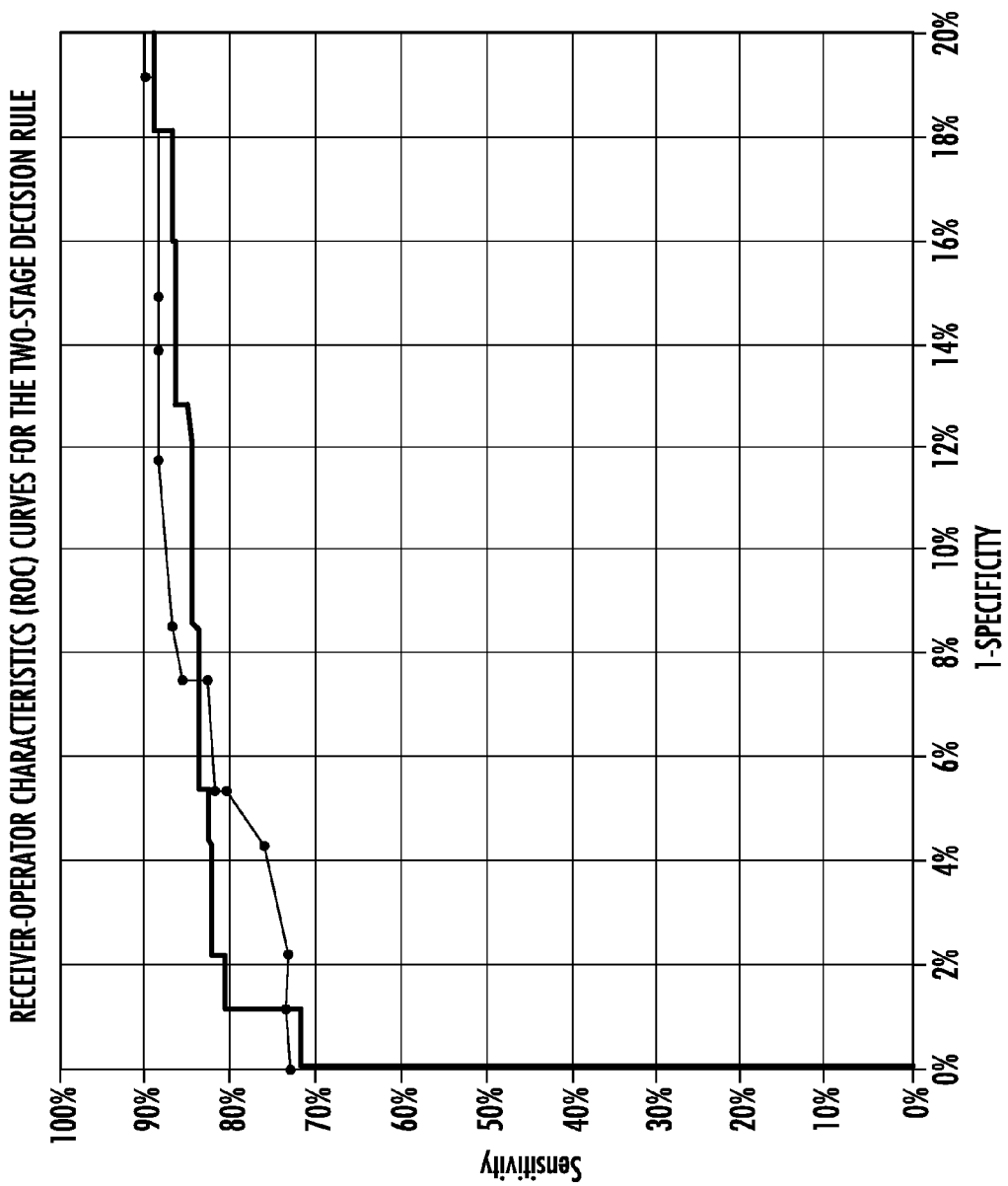
FIG. 4 is a graph showing Receiver-Operator Characteristic (ROC) curves for the two-stage decision rule using the four genes with 100% specificity in the first stage, and a logistic regression combination in the second. ROCs are used to assess the diagnostic value of tests using a single numerical cut-off value. ROC curves show the true-positive rate (sensitivity) plotted against the false-positive rate (1-specificity). This allows one to trace the relationship between the true positive rate against the false positive rate. The thin line is an ROC based on a logistic score using binary dichotomization of the genes at zero/nonzero methylation levels. The thick line is an ROC based on logistic score using the actual log methylation levels.
Figure 5:
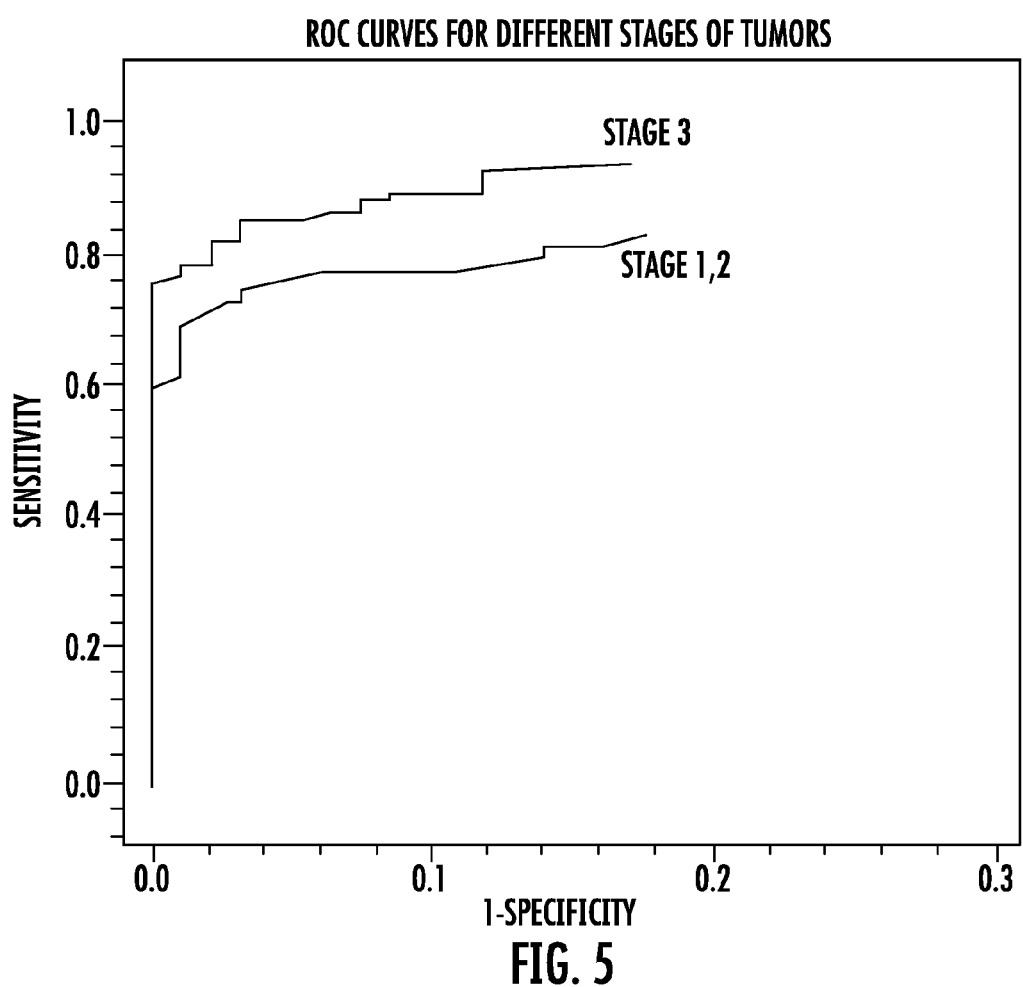
FIG. 5 shows ROC curves for different stage tumors. Non-muscle invasive [Stage 1: pTa, pTis; Stage 2: pT1] and muscle invasive tumors (Stage 3: ≥pT2) were detected by 75% and 85% respectively by QMSP with high specificity (i.e. near 96%). The curves are internally validated ROC, adjusted for over-fitting.

FIG. 3 describes the combined two-stage algorithm used for classification. The operating characteristics of the two-stage approach was based on four markers with perfect specificity followed by logistic regression analysis on the remaining five markers as shown in FIG. 4. Sixty nine percent of bladder cancer patients were correctly diagnosed by incorporating four genes (p16, ARF, MGMT, and GSTP1) with 100% specificity (FIG. 4). Addition of a logistic regression score based on the remaining five genes to the latter four genes improved sensitivity while decreasing specificity (FIG. 4). Sensitivity was increased to 82% with a decrease in specificity to 96%. The overall Receiver-Operator Characteristic (ROC) curve was compared to that obtained by adding each of the genes individually. As expected, individual genes contributed less and a 10% to 20% improvement in sensitivity was observed when any of the five genes (APC, TIMP3, CDH1, RARβ2 and RASSF1A) were added to four genes (p16, MGMT, ARF and GSTP1) to obtain 100% specificity. The logistic model confirmed improvement in sensitivity as additional genes were added to the four genes with perfect specificity. FIG. 5 shows how the combined logistic score model performs at different tumor stages. The sensitivity increased with stage, ranging from 75% sensitivity for non-muscle invasive tumors to 85% sensitivity for muscle invasive tumors detectable by QMSP with high specificity (96%) (FIG. 5).

Figure 6:
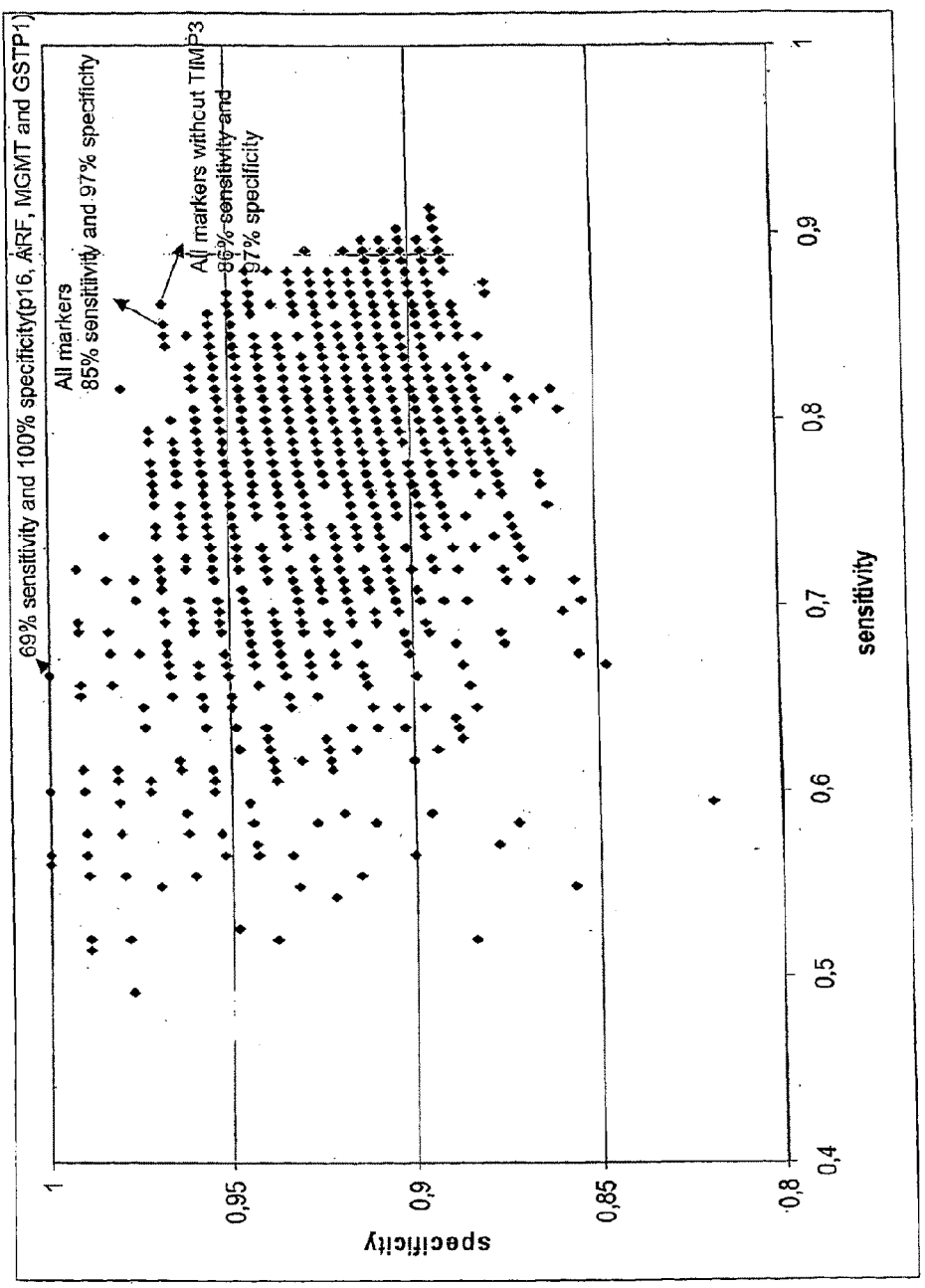
FIG. 6 is a graph showing the global sensitivity and specificity of selected tests from 511 different combinations using nine markers. Five different learning sets L1/L2/L3/L4/L5 were generated based on different cut points selected on individual ROC curves. Five different analytical methods were used to determine the accuracy of the tests. The data shown here are based on the Bayesian Network analysis. Arrows indicate some of the most promising tests.

In addition to the latter statistical model, a Bayes Network statistical approach was applied (Data Mining: Practical machine learning tools with Java implementations," by Ian H. Witten and Eibe Frank, Morgan Kaufmann, San Francisco, 2000 with the additional advantage of providing a distribution over possible models instead of a single best model and using optimal cutoffs from learning set for each gene. A general overview of the performance of QMSP (quantitative methylation specific PCR) as a diagnostic test based on multiple different combinations of all nine genes is shown at FIG. 6 (Global sensitivity and specificity). FIG. 6 shows the sensitivity and specificity pairs of all rules evaluated, and points on the boundaries represent the theoretical maximum performance of any statistical rule. The logistic rule utilized here comes quite close to these optimum performance levels, but its sensitivity is several percentage points lower for the same specificity. The former rules, which are quite complex, represent biologic reality.

Several clinicopathological and demographic parameters (age, gender, tumor stage, tumor grade, cytology, cystoscopy, metastasis, invasion, smoking and drinking alcohol) were compared with the methylation patterns developed in the urine DNA. Contingency table and logistic regression analysis was performed to determine whether the frequency of QMSP markers or the combination thereof correlated with parameters associated with bladder cancer prognosis. Tumor grade, Tumour, Node, Metastasis stage, metastasis, cytology, cystoscopy and invasiveness correlated with single and multimarker methylation (Table 3).

TABLE 3

Correlation of clinical parameters and epigenetic alterations

| | Markers | | | | | | | | |
|---|---|---|---|---|---|---|---|---|---|
| Parameters | APC | ARF | CDH1 | GSTP1 | MGMT | P16 | RARβ2 | RASSF1A | TIMP3 |
| Higher grade | NS | NS | NS | NS | NS | NS | NS | NS | NS |
| Higher stage | NS | *p = 0.02 OR 2.4(1.1-4.8) | NS | NS | *p = 0.03 OR (1.06-3.9) | NS | NS | NS | NS |

TABLE 3-continued

Correlation of clinical parameters and epigenetic alterations

| Parameters | APC | ARF | CDH1 | GSTP1 | MGMT | P16 | RARβ2 | RASSF1A | TIMP3 |
|---|---|---|---|---|---|---|---|---|---|
| Metastasis present | NS | NS | NS | NS | NS | NS | NS | NS | *p = 0.05 OR 2.0(.99-4.2) |
| Invasive | NS | *p = 0.01 OR 3.5(1.5-8.5) | NS | *p = 0.01 OR 2.5(1.2-4.8) | *p = 0.01 OR 2.8(1.3-6.0) | NS | NS | NS | *p = 0.05 OR 2.0(1.0-4.0) |
| Drinker | NS | NS | NS | NS | NS | NS | NS | NS | NS |
| Smoker | NS | NS | NS | NS | NS | NS | NS | NS | NS |
| Cytology positive | NS | NS | NS | *p = 0.004 OR 2.9(1.4-5.8) | NS | NS | NS | *p = 0.05 OR 1.99(0.99-4.0) | NS |
| Cytoscopy positive | *p = 0.01 OR 2.6(1.23-5.5) | *p = 0.05 Or 2.6(1.0-6.8) | *p = 0.05 | NS | NS | NS | NS | *p = 0.03 OR 2.24(1.1-4.7) | *p = 0.05 OR 2.2(0.99-4.8) |

*p = <0.05: significant
NS = not significant. Higher grade = grade 3; Higher stage = ≥pT2

Using univariate analysis, ARF and MGMT methylation significantly correlated [(OR 2.4, 95% CI 1.1-4.8 and OR 2.0, CI 1.0-3.9) respectively] with increasing T stage. Methylation of ARF [OR 3.5, 95% CI 1.5-8.5]; MGMT [OR 2.8, CI 1.3-6.0]; GSTP1 [OR 2.5, CI 1.2-4.8] and TIMP3 [OR 2.0, CI 1.0-4.0] significantly correlated with tumor invasiveness (Table 3). GSTP1 [OR 2.9, 95% CI 1.4-5.8] and Rassf1A [OR 1.9, 95% CI (0.9-4.0)] methylation significantly correlated with cytology positive cases. A further summary of clinical parameters and epigenetic alterations is detailed in Table 3. Aberrant methylation in urine sediment DNA of bladder cancer patients had no correlation with other clinical and demographic data, including age and gender, histological subtype and recurrence of tumor.

Finally, correlation analysis between all pairs of markers (Table 4) was performed.

TABLE 4

Spearman Correlation matrix among methylation levels of all genes.

| Markers | APC | ARF | CDH1 | GSTP1 | MGMT | p16 | RAR_beta | Rassf1a | TIMP3 |
|---|---|---|---|---|---|---|---|---|---|
| APC | 1.00 | 0.37 | 0.54 | 0.45 | 0.41 | 0.38 | 0.48 | 0.54 | 0.41 |
| ARF | | | 0.55 | 0.40 | 0.48 | 0.31 | 0.26 | 0.36 | 0.53 |
| CDH1 | | | | 0.41 | 0.49 | 0.42 | 0.42 | 0.51 | 0.55 |
| GSTP1 | | | | | 0.40 | 0.43 | 0.30 | 0.52 | 0.28 |
| MGMT | | | | | | 0.45 | 0.42 | 0.34 | 0.34 |
| p16 | | | | | | | 0.44 | 0.39 | 0.25 |
| RAR_beta | | | | | | | | 0.44 | 0.40 |
| Rassf1a | | | | | | | | | 0.43 |
| TIMP3 | | | | | | | | | 1.00 |

*All correlations had p < 0.001.

Methylation of every pair was statistically significantly correlated. The strongest correlations (r>0.50) were between CDH1 and APC, ARF, Rassf1a and TIMP3. In addition, TIMP3 and ARF, and GSTP1 and RASSf1a were highly correlated. In sum, 75% of superficial bladder tumors were detected in our study (FIG. 5). All of the 15 primary tumors tested harbored at least 1 methylated marker. Therefore, the failure to detect methylation is likely attributable to the lack of representative cancer cells or shed DNA in the urine sediment for those tumors that were missed.

In the present study, each gene was amplified individually. Genetic analysis using multiplex PCR with genes specific for bladder cancer can also be used. Recent developments in hardware and software applications for automated signal enumeration and robotic pipeting facilitate the use of genetic marker sets as diagnostic tools in pathological laboratories.

Cystoscopy is considered the gold standard for bladder cancer diagnosis and offers the potential to both find and remove small lesion, but it is associated with high cost, patient discomfort, and variable sensitivity. The conventional Methylation-Specific PCR (MSP) assay is a particularly sensitive technique for the purpose of detecting occult cancer cells in plasma, serum, lymph nodes and broncoalveolar lavage of different cancer types (Harden et al., Clin Cancer Res 2003; 9:1370-5; Data Mining: supra; Cairns et al., Nat Genet 1995; 11:210-2; Ahrendt et al., J Natl Cancer Inst 1999; 91:332-9; Kawakami et al., J Natl Cancer Inst 2000; 92:1805-11; Cancer Res 2004 Sep. 15; 64(18):6476-81). Quantitative analysis of DNA products is critical in the reproducible interpretation of results. The Quantitative (QMSP) assay provides a highly sensitive automated approach. This assay also allows identification of 1 methylated allele in the presence of more than one thousand unmethylated alleles.

Specificity is enhanced by hybridization with a labeled internal probe to the specific MSP product. QMSP may additionally enhance detection over single-marker methods by incorporating a panel of methylation markers to account for tumor cell heterogeneity that may exist between patients, as well as between the primary tumor, adjacent margin and metastasis. Some patients lacked detectable methylated DNA in their urine despite the presence of methylation in the primary tumor. This may have occurred because the cancers did not spill significant amounts of neoplastic DNA into the patient's urine at the time of sample collection. Alternatively, methylated markers may have been present in the urine sediment samples at levels below the level of detection of the QMSP assay of the invention. This alternative seems unlikely given that the assay can detect as few as fifteen copies in a PCR reaction (equivalent to approximately 8 cells). This level of sensitivity is similar to that reported by others (Millar et al., Methods 2002; 27:108-13). Increasing the amount of input DNA might overcome this problem. Methylation specific PCR does involve an additional chemical modification of DNA using bisulfite to modify unmethylated cytosines into thymines (Millar et al., supra). The bisulfite modification also results in DNA breakage perhaps lowering the sensitivity of MSP relative to ordinary PCR.

Using four-methylation markers, p16, MGMT, GSTP1 and ARF, methylation of at least one marker in most (69%) of bladder cancer patients was identified. Concordant hypermethylation of TIMP3 and ARF was found in urine sediment DNA from bladder cancer patients and Rassf1A was strongly correlated with APC, CDH1 and GSTP1. A possible interaction between these genes in bladder cancer deserves further evaluation. Interestingly, GSTP1 and Rassf1A methylation were associated with urine cytology positive cases suggesting that the methylation of these markers may be reflected in cell morphology.

The relative methylation values for each marker varied widely among urine specimens of cancer patients. These results were expected due to the heterogeneity and number of tumor cells in each urine sediment. The results reported herein suggest that increasing the number of markers in a neoplasia screening panel increases sensitivity. Additional marker identification is underway for bladder cancer using a strategy used to unmask silenced genes in esophageal cancer (Yamashita et al., Cancer Cell 2002; 2:485-95), which is hereby incorporated by reference in its entirety.

Current methods approved by the FDA for the diagnosis of bladder cancer include ell based and protein assays. Such assays show inferior sensitivity and specificity when compared to the QMSP assay reported here. Direct comparisons of the present assay with conventional assays in prospective studies remains to be done. In addition, some of the methylation markers used in our assay, have been tested individually or in a limited panel, for detection and association with tumor progression in some studies in primary bladder cancer and in urine (Maruyama et al., Cancer Res 2001; 61:8659-63; Salem et al., Cancer Res 2000; 60:2473-6; Dominguez et al., Clin Cancer Res 2002; 8:980-5; Horikawa et al., J Urol 2003; 169:1541-5; Dulaimi et al., Clin Cancer Res 2004; 10:1887-93) by conventional MSP. Markers associated with invasion, which are listed in Table 3, are likely to mark tumors associated with a poor prognosis. The presence of such markers indicates that patient's having neoplasias associated with such markers should be treated with early aggressive treatment.

The use of methylation markers is useful for the molecular diagnosis of bladder cancer. Urine testing will also likely provide complementary information to enhance current methods for staging disease. In addition, testing for relevant epigenetic markers in voided urine is useful for the early detection of bladder cancer and individualized therapeutic strategies.

Example 2

Renal Carcinoma

Epigenetic alterations, including changes in the status of DNA methylation, are one of the most common molecular alterations in renal cancer (Romanenko et al., Diag. Mol. Pathol. 11: 163-9, 2002; Bachman et al., Cancer Res, 59: 798-802, 1999; Nojima et al., Mol Carcinog, 32:19-27, 2001; Kawakami et al., Urology, 61: 226-30, 2003; Wagner et al., Oncogene, 21:7277-82, 2002; Esteller et al., Cancer Res, 58: 4515-8, 1998). Cytosine methylation occurs after DNA synthesis by enzymatic transfer of a methyl group from the methyl donor S-adenosylmethionine to the carbon-5 position of cytosine. Cytosines are methylated in the human genome almost exclusively when located 5' to a guanosine. Regions with a high G:C content (so-called CpG islands) are mostly unmethylated in normal tissue but may be methylated to varying degrees in human cancers, thus representing tumor-specific alterations (Jones et al., Nat Rev Genet, 3: 415-28, 2002; Laird et al., Nat Rev Cancer, 3: 253-66, 2003). The presence of abnormally high DNA concentrations in the serum and urine of patients with various malignant diseases has been confirmed during the past decade (Ngan et al., Ann N Y Acad Sci, 945: 73-9, 2001; Lo Y M. et al., Biomed Pharmacother, 55: 362-5, 2001; Sidransky et al., Science, 252: 706-9, 1991). Some studies recently have reported DNA in the serum and urine of renal cancer patients at diagnosis (Eisenberger et al., J Natl Cancer Inst, 91: 2028-32, 1999; Gonzalgo et al Clin Cancer Res, 8: 1878-81, 2002). The presence of methylated DNA in the bodily fluids of patients with various types of malignancies and the absence of methylated DNA in normal control patients has also been reported (Sanchez-Cespedes-et al., Cancer Res, 60: 892-5, 2000; Esteller et al., Cancer Res, 59: 67-70, 1999; Topaloglu et al., Clin Cancer Res, 10: 2284-8, 2004). To date, most studies detecting hypermethylation rely on conventional methylation specific PCR (MSP), a sensitive but not quantitative assay. Using quantitative methylation-specific PCR (QMSP) advantageously defines a cutoff point between cancer and control groups.

DNA methylation-based markers in pretherapeutic urine and serum DNA from renal cancer patients were analysed to evaluate the diagnostic efficacy of QMSP for renal cell carcinoma. As reported in more detail below, the tumor and the matched urine and serum DNA for aberrant methylation of nine gene promoters (CDH1, APC, MGMT, RASSF1A, GSTP1, p16, RAR-β2, and ARF) from seventeen patients with primary kidney cancer was analysed using quantitative fluorogenic real-time PCR. Nine additional (twenty-six urine sediments total) urine sediments and 1 serum sample (18 serum samples total) from renal cancer patients without matched tumor tissue were also examined. Ninety-one urine samples from patients without genitourinary cancer and thirty serum samples from patients without cancer served as controls. Promoter hypermethylation of at least two of the genes studied was detected in sixteen (94%) of seventeen primary tumors. Aberrant methylation in urine and serum DNA generally was accompanied by methylation in the matched tumor samples. Urine samples from ninety-one control subjects without evidence of genitourinary cancer revealed no methylation of the MGMT, GSTP1, p16, and ARF genes, whereas methylation of RAR-β2, RASSF1A, CDH1, APC, and TIMP3 was detected at low levels in a few control subjects.

Overall, twenty-three (88%) of twenty-six urine samples and twelve (67%) of eighteen serum samples from cancer patients were methylation positive for at least one of the genes tested. By combination of urine or serum analysis of renal cancer patients, hypemethylation was detected in sixteen of seventeen patients (94% sensitivity) with high specificity. These results indicate that promoter hypermethylation in urine or serum can be detected in the majority of renal cancer patients. This noninvasive high-throughput approach can be used for the early detection and surveillance of renal cancer.

Frequency of Methylation in Primary Kidney Tumors.

Figure 7:
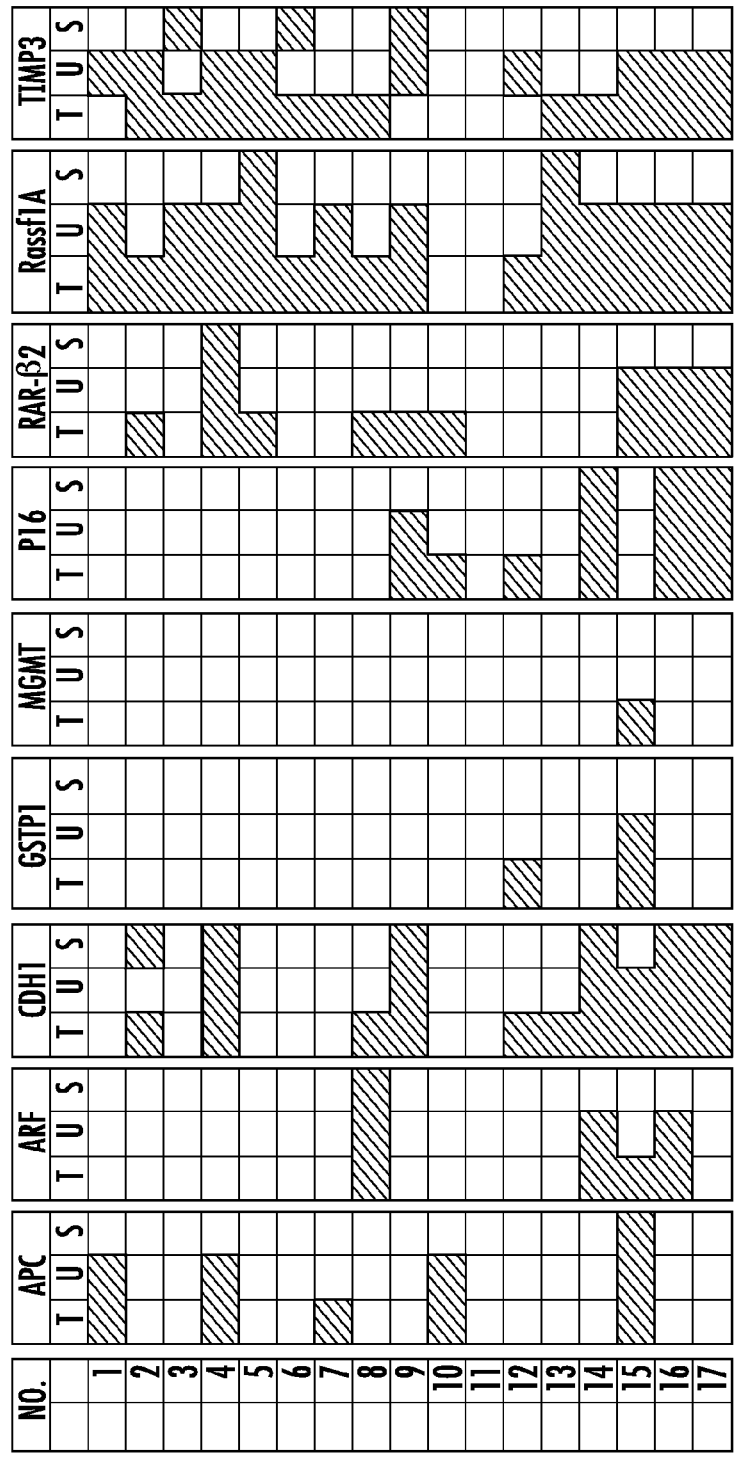
FIG. 7 shows a summary of methylation states of GSTP1, ARF, P16, MGMT, RARβ2, TIMP3, CDH1, APC, and RASSF1A in seventeen primary tumors (T) and matched urine (U) and serum (S) samples. Black boxes represent samples that are methylated; white boxes represent samples without methylation.
Figure 8E:
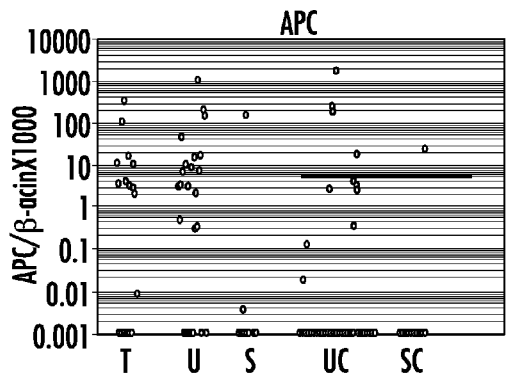
Figure 8F:
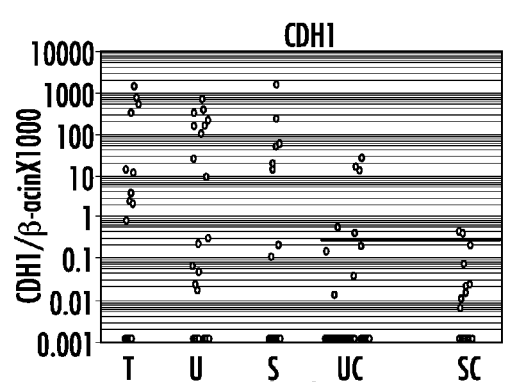
Figure 8G:
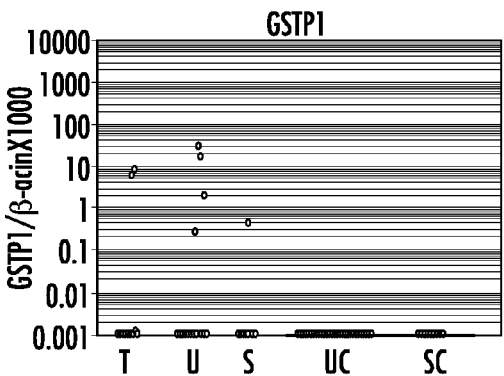
Figure 8H:
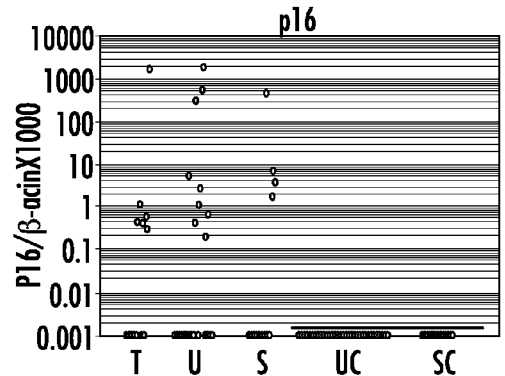
Figure 8I:
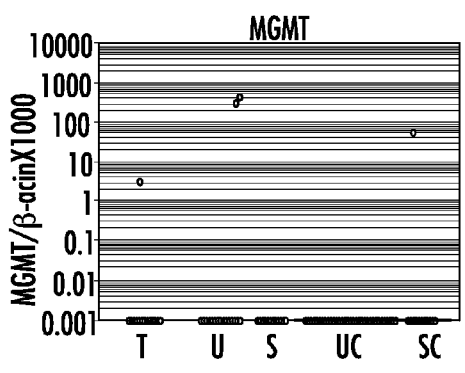

Paired urine and serum specimens from patients with cancer and control subjects were examined by QMSP for nine genes having diverse functions, including cell cycle regulation, metastatic suppression, tumor suppression, and DNA repair. Aberrant promoter hypermethylation of at least two of the genes was detected in sixteen of seventeen patient samples (94%) obtained from patient's with malignant tumors of the kidney. Thirteen of seventeen patient samples (76%) were positive for at least three genes simultaneously (Table 5; FIG. 7).

TABLE 5

Samples showing methylation in tumor, urine, and serum

| No. | Pathology[a] | Age (y) | Sex | pTNM[b] | Grade[c] | Symptoms/history | Methylation tumor/urine/serum[d] |
|---|---|---|---|---|---|---|---|
| 1 | RCC, clear cell | 70 | M | T1NXMX | I-II | None | 2/3/0 |
| 2 | RCC, clear cell | 33 | M | T2NXMX | I | Hematuria/pain | 4/1/1 |
| 3 | RCC, clear cell | 59 | M | T2NXMX | I | None | 2/1/1 |
| 4 | RCC, clear cell | 58 | M | T2NXMX | II/IV | CIS of glans, pain, choleliathesis | 5/5/2 |
| 5 | RCC, clear cell | 74 | F | T2NXMX | II | Glomerulosclerosis | 3/2/1 |
| 6 | RCC, clear cell | 61 | F | T2N0MX | II | None, renal pelvis involved | 2/0/1 |
| 7 | RCC, clear cell | 65 | M | T3aNXMX | II | Discomport | 3/1/0 |
| 8 | RCC, papillary | 70 | M | T2NXMX | III | None, collecting duct involved | 5/1/0 |
| 9 | RCC, clear cell | 45 | M | T2NXMX | I | None | 4/4/2 |
| 10 | RCC, clear cell | 72 | M | T3aNXMX | III | None | 3/1/0 |
| 11 | RCC, clear cell | 46 | F | T2NXMX | II-III | None | 0/0/0 |
| 12 | RCC, clear cell | 65 | M | T3bN0M1 | III | Metastasis (lung, subcutaneous) | 4/1/0 |
| 13 | RCC, clear cell | 60 | M | T2M0NX | II | None | 3/2/1 |
| 14 | RCC, chromoprobe | 52 | M | T2N0MX | II-III | Microscopic hematuria | 5/4/2 |
| 15 | RCC, clear cell | 75 | M | T2NXMX | II | Recurrent UTI, hematuria | 8/6/1 |
| 16 | RCC, clear cell | 61 | M | T2NXMX | II | Hematuria | 6/6/2 |
| 17 | RCC, clear cell | 51 | M | T2N0MX | II-III | Hematuria | 5/5/2 |
| 18 | RCC, clear cell | 60 | F | T1N0MX | I-II | Discomfort | ND/3/1 |
| 19 | RCC, clear cell | 69 | F | NA | II/IV | Hematuria | ND/4/ND |
| 20 | RCC, clear cell | 55 | M | pT2, Nx, MX | I-II/IV | Pain | ND/4/ND |
| 21 | Collecting duct carcinoma | 61 | F | pT3 N1 MX | NA | Lyme disease | ND/2/ND |
| 22 | RCC, clear cell | 63 | F | pT2, Nx, MX | NA | Hematuria | ND/8/ND |
| 23 | RCC, clear cell | 68 | M | NA | III | Pain and microscopic hamaturia | ND/6/ND |
| 24 | RCC, clear cell | 65 | F | T3b Nx MX | IV/IV | Recurrent UTI, hematuria pain | ND/5/ND |
| 25 | RCC, clear cell | 81 | M | PT3NXMX | III/IV | Nocturia | ND/0/ND |
| 26 | RCC, clear cell | 54 | F | NA | NA | NA | ND/5/ND |

In one patient (Patient 11), no methylation was detected in any gene promoter. The frequency of aberrant methylation in all of the types of samples and median methylation values (gene/β-actin×1000) for each gene in tumor, urine, serum, and control DNA are shown in Table 6 (below).

TABLE 6

Frequency of methylation based on different cutoff points and median values in clinical samples

| Markers | Methylation positive % (number of methylation positive/number of total cases) | | | | | Cutoff values | Median | | | | |
|---|---|---|---|---|---|---|---|---|---|---|---|
| | Tumor | Urine (cancer) | Serum (cancer) | Urine (control) | Serum (control) | | Tumor | Urine (cancer) | Serum (cancer) | Serum (control) | Urine (control) |
| APC | 29% (5/17) | 38% (10/26) | 6% (1/18) | 4% (4/91) | 3% (1/30) | 4.5 | 2.89 | 2.95 | 0 | 0 | 0 |
| ARF | 24% (4/17) | 31% (8/26) | 6% (1/18) | 0% (0/91) | 3% (1/30) | 0 | 0 | 0 | 0 | 0 | 0 |
| CDH1 | 59% (10/17) | 38% (10/26) | 33% (6/18) | 5% (5/91) | 7% (2/30) | 0.3 | 0.28 | 0.23 | 0 | 0 | 0 |
| CSTP1 | 12% (2/17) | 15% (4/26) | 6% (1/18) | 0% (0/91) | 0% (0/30) | 0 | 0 | 0 | 0 | 0 | 0 |
| MGMT | 6% (1/17) | 8% (2/26) | 0% (0/18) | 0% (0/91) | 3% (1/30) | 0 | 0 | 0 | 0 | 0 | 0 |
| p16 | 35% (6/17) | 35% (9/26) | 22% (4/18) | 0% (0/91) | 0% (0/30) | 0 | 0 | 0 | 0 | 0 | 0 |
| RAR-β2 | 53% (9/17) | 31% (8/26) | 6% (1/18) | 9% (8/91) | 0% (0/30) | 0.1 | 0 | 0 | 0 | 0 | 0 |
| RASSF1A | 88% (15/17) | 65% (17/26) | 11% (2/18) | 11% (10/91) | 3% (1/30) | 0.1 | 10.9 | 9 | 0 | 0 | 0 |
| TIMP3 | 71% (12/17) | 46% (12/26) | 17% (3/18) | 9% (8/91) | 0% (0/30) | 1 | 1.92 | 0.02 | 0 | 0 | 0 |

Methylation frequencies for the five genes (APC, CDH1, RAR-β2, RASSF1A, and TIMP3) with cutoff points >0 was also determined.

TABLE 7

Frequency of methylation of 5 genes based on zero cut off points

| Markers | Methylation positive %(Number of methylation positive/Number of total cases | | | | Cut off values |
|---|---|---|---|---|---|
| | Tumor | Urine (Cancer) | Serum (Cancer) | Urine (Control) | Serum (Control) | |
| APC | 65%(11/17) | 65%(17/26) | 11%(2/18) | 12%(11/91) | 3%(1/30) | 0 |
| CDH1 | 59%(10/17) | 62%(16/26) | 44%(8/18) | 10%(9/91) | 30%(9/30) | 0 |
| RARβ2 | 59%(10/17) | 42%(11/26) | 6%(1/18) | 12%(11/91) | 0%(0/30) | 0 |
| Rassf1A | 88%(15/17) | 69%(18/26) | 11%(2/18) | 11%(10/91) | 3%(1/30) | 0 |
| TIMP3 | 82%(14/17) | 58%(15/26) | 17%(3/18) | 14%(13/91) | 3%(1/30) | 0 |

In the kidney tumor samples, frequent methylation was detected in RASSF1A (88%), TIMP3 (71%), CDH1 (590%), RAR-β2 (53%), p16 (35%), ARF (24%), and APC (29%). Methylation of GSTP1 and MGMT was much less common, 12% and 6%, respectively. Aberrant methylation in primary kidney tumors had no correlation with patient demographic data, including age and gender, histologic subtype, and staging of the tumor.

Methylation in Urine and Serum DNA.

The matching seventeen urine and serum samples from these kidney cancer patients were tested for methylation. An additional nine urine samples and one serum sample from renal cancer patients (without matched primary tumor) were included in this study. The analytical and clinical sensitivity of individual genes is shown in Table 8 (below).

TABLE 8

Sensitive detection of cancer in urine sediment and serum DNA of RCC patients using DNA methylation markers

| Disease | DNA source | Markers | Analytical sensitivity (%) | Clinical sensitivity (%) | Specificity (%) | Cutoff values |
|---|---|---|---|---|---|---|
| Renal cancer | Urine | APC | 4/5 (80) | 10/26 (38) | 96 | 4.5 |
| | | ARF | 3/4 (75) | 8/26 (31) | 100 | 0 |
| | | CDH1 | 6/10 (60) | 10/26 (38) | 95 | 0.3 |
| | | GSTP1 | 1/2 (50) | 4/26 (15) | 100 | 0 |
| | | MGMT | 0/1 (0) | 2/26 (8) | 100 | 0 |
| | | p16 | 4/6 (67) | 9/26 (35) | 100 | 0 |
| | | RAR-82 | 4/9 (44) | 8/26 (31) | 91 | 0.1 |

TABLE 8-continued

Sensitive detection of cancer in urine sediment and serum
DNA of RCC patients using DNA methylation markers

| Disease | DNA source | Markers | Analytical sensitivity (%) | Clinical sensitivity (%) | Specificity (%) | Cutoff values |
|---|---|---|---|---|---|---|
| | | RASSF1A | 11/15 (73) | 17/26 (65) | 89 | 0.1 |
| | | TIMP3 | 6/12 (50) | 12/26 (46) | 91 | 1 |
| | Serum | APC | 1/5 (20) | 1/18 (6) | 97 | 4.5 |
| | | ARF | 1/4 (25) | 1/18 (6) | 97 | 0 |
| | | CDH1 | 6/10 (60) | 6/18 (33) | 93 | 0.3 |
| | | GSTP1 | 0/2 (0) | 1/18 (6) | 100 | 0 |
| | | MGMT | 0/1 (0) | 0/18 (0) | 97 | 0 |
| | | p16 | 3/6 (50) | 4/18 (22) | 100 | 0 |
| | | RAR-β2 | 1/9 (11) | 1/18 (6) | 100 | 0.1 |
| | | RASSF1A | 2/15 (13) | 2/18 (11) | 97 | 0.1 |
| | | TIMP3 | 2/12 (17) | 3/18 (17) | 100 | 1 |

Overall, twenty-three of twenty-six (88%) cancer patients were methylation positive in urine sediment DNA for at least one of the nine genes tested (Table 5; FIG. 7). Urine DNA was negative in all of the 91 control subjects with no history of genitourinary neoplasm in four genes examined p16, MGMT, GSTP1, and ARF). CDH1, RASSF1A, TIMP3, RAR-β2, and APC showed varying levels of methylation in some of the control urine sediment samples. For these five genes, optimal cutoff value was set (Table 7; FIGS. 8A-8I) to obtain the highest sensitivity and specificity. The analytical and clinical sensitivities of each gene with defined cutoff values are detailed in Table 8. Three urine samples harbored methylated TIMP3 in the absence of methylation in the matched primary tissue. In nearly all cases, however, the identical methylation pattern was found between primary tumor and matched urine DNA samples as shown in FIG. 7. No correlation was identified between the methylation index (total number of genes methylated/total number of genes analyzed) and any of the clinicopathologic characteristics (i.e., tumor type, grade, and stage in urine sediment samples; data not shown).

Analytical sensitivity, which is defined as the fraction of cases in which methylation of a marker is found in urine or serum for cases with confirmed methylation of the same marker in the associated tumor (e.g., in Table 6, the frequency of APC methylation in primary tumors is 29% (5/17); of these five methylated cases, methylation was detected in the urine of 4 patients; therefore, the analytical sensitivity is 80% (⅘)). "Clinical sensitivity" is defined as the fraction of confirmed cases of disease in which methylation of a marker was found in urine or serum, regardless of whether methylation of that marker was present in the associated tumor or regardless of whether the associated tumor was analyzed for the presence of the marker. Cases in which urine or serum were not analyzed were excluded from both sensitivity calculations. "Specificity" is defined as the fraction of controls without the disease that show a lack of detectable methylation in urine or serum.

In serum DNA, twelve of eighteen (67%) patients were methylation positive for at least one of the genes tested (FIG. 7; Table 5). The frequency of aberrant promoter methylation detected in matched serum for each marker was 20% (1 of 5) for APC, 25% (1 of 4) for ARF, 60% (6 of 10) for CDH1, 0% (0 of 2) for GSTP1, 0% (0 of 1) for MGMT, 50% (3 of 6) for p16, 11% (1 of 9) for RAR-β2, 13% (2 of 15) for RASSF1A, and 17% (2 of 12) for TIMP3. Methylation was detected in one serum sample for TIMP3 without evidence of methylation in the primary tumor. None of the thirty controls displayed promoter hypermethylation in any of the four genes examined (p16, RAR-β2, TIMP3, and GSTP1) in serum. Two of the control sera displayed methylation of CDH1 at low levels (3.1 and 3.6; cutoff value for CDH1 was 0.3). MGMT, APC, RASSF1A, and ARF displayed methylation in one sample each at reasonably high level. Interestingly, all of the six control patients who displayed serum methylation above the cutoff values were smokers. No serum methylation was detected in the nonsmoker control group. The specificity, clinical sensitivity, analytical sensitivity, and cutoff points are summarized in Table 7.

Advances in basic research have shed light on key alterations that contribute to the development of renal neoplasia. Detailed studies of pathology have underscored the morphologic heterogeneity of renal cancers (Thoenes et al., Pathol Res Pract, 181: 125-43, 1986). Genetic and epigenetic studies using a variety of technologies have shown that renal cancers are characterized by specific genetic and epigenetic alterations (e.g., loss of heterozygosity at the VHL locus (Gnarra et al., Nat Genet, 7: 85-90, 1994), and hypermethylation of RASSF1A, TIMP3, p16, GSTP1, and CDH1 (Romanenko et al., Diagn Mol Pathol, 11: 163-9, 2002; Bachman et al., Cancer Res, 59: 798-802, 1999; Nojima et al., Mol Carcinog, 32: 19-27, 2001; Wagner et al., Oncogene, 21: 7277-82, 2002; Esteller et al., Cancer Res, 58: 4515-8, 1998; Dreijerink et al., Proc Natl Acad Sci USA, 98: 7504-9, 2001). Using the same set of samples, microsatellite analysis of urine DNA detected the presence of malignancy in patients with clinically organ-confined renal cancer (Eisenberger et al., J Natl Cancer Inst, 91: 2028-32, 1999). In the present study, 94% of primary kidney tumors harbored CpG island hypermethylation in at least two of nine cancer-related genes. Eighty-eight percent of patients with aberrant methylation in primary tumors also exhibited hypermethylation in urine DNA. Because there were some false-positive results for TIMP3, a 76% sensitivity was found using only the remaining eight genes. Heterogeneity of neoplastic cells in urine and tumor foci may contribute to this. Conversely, TIMP3 methylation may be a feature of non-neoplastic tissues which may limit its value as a diagnostic marker for renal neoplasia. Excluding TIMP3, detection of promoter methylation in the urine of renal cancer patients was a specific event: (a) overall aberrant methylation was not detected in any of the ninety-one age-matched control urine samples with the exception of low levels in five genes; and (b) the identical methylation profiles were found in the corresponding tumor; aberrant methylation was not detected in the urine of kidney cancer patients without methylation in the corresponding tumor.

The development of real-time PCR has simplified the study of genes inactivated by promoter hypermethylation in human cancer. It is a highly sensitive assay that is capable of detecting methylated alleles in the presence of a 1000-fold excess of unmethylated alleles. QMSP is likely to be more sensitive than conventional MSP depending on the promoter, primers, and PCR conditions used. On the basis of conventional MSP, methylated p16 alleles in the primary renal cell carcinoma were detected from 20-32% (Romanenko et al., Diagn Mol Pathol, 11: 163-9, 2002). In the present study, p16 was methylated in 35% of primary tumors and in 67% and 50% of matched urine and serum samples, respectively.

Methylation was not identified in any of the nine genes tested in Patients 11 and 25. Eventual identification of new renal cancer-specific tumor suppressor genes and their genetic and epigenetic studies may provide additional markers for such patients. Interestingly, in one of these cases (Patient 11; pT2, grade II-III) a loss of heterozygosity was identified in only one microsatellite marker in the tumor, and no loss of heterozygosity or microsatellite instability was detected in the matched urine and serum samples. These results suggest that some kidney tumors do not generate or contribute sufficient DNA into the urine for analysis.

Several studies using different approaches have demonstrated promoter hypermethylation of CDH1 (67%), RASSF1A (44-91%), p16 (20-32%), GSTP1 (20%), and TIMP3 (78%) in primary renal tumor tissue (Romanenko supra; Bachman supra; Nojima supra; Kawakami supra; Wagner supra; Esteller supra; Dreijerink supra). A similar frequency of methylation is reported herein for all of these genes, including RASSF1A (88%), CDH1 (59%), TIMP3 (71%), and GSTP1 (12%) in primary kidney tumors. To our knowledge, methylation of MGMT, RAR-β2, APC, and ARF was not previously tested in renal cancer. The promoter of the latter three genes harbored frequent methylation in primary tumors. The value of MGMT (6% methylation) may limit its use as a marker for kidney cancer. The present study identified an optimal panel of methylation markers with high sensitivity and specificity that can be used for the screening of patient samples for neoplasia. Moreover, given the recent development of new high-throughput platforms, the use of such panels is now requires no more than routine methods.

The detection of tumor molecular signatures in body fluids has implications for the identification of high-risk subjects, patients with preinvasive or early stage lesions, and for monitoring residual disease in patients that have been treated for a neoplasia. Molecular approaches characterized by a high specificity have in the past had variable sensitivity, perhaps because of the presence of low tumor DNA quantities in urine or serum or because of a high level of contamination with normal DNA. Several approaches to improve assay sensitivity have been applied to tumor tissue, plasma, sputum, stool, and bronchoalveolar lavage samples. Sensitivity has been improved over conventional MSP by performing a semi-nested MSP after a DNA preamplification step (Kersting et al., J Clin Oncol, 18: 3221-9, 2000) or a nested two-stage PCR with a concomitant reduction in specificity and lack of quantitation [(Palmisano et al., Cancer Res, 60: 5954-8, 2000). The sensitivity and specificity of QMSP when used in combination with (a) the isolation of neoplastic cells or DNA from the urine by antibody or oligo-based magnetic bead technology before DNA extraction; and (b) increasing the number of renal cancer-specific markers overcomes the drawbacks of previous molecular methods.

Moreover, the QMSP assay described herein provides several distinct advantages over conventional MSP: (a) omission of all of the postamplification steps reduces the risk of contamination and increases the throughput of the system; (b) the assay is more stringent and more specific because in addition to the two PCR primers, the fluorescent-labeled hybridization probe has to anneal correctly between the two primers; (c) the assay is quantitative, automated, and readily adaptable to clinical setting and screening studies; and (d) the assay is amenable to multiplex amplification for the analysis of panels in clinical samples. At present, four different dyes were used for the amplification of four distinct markers. Increasing the number of dyes used for QMSP will enhance the multimarker diagnostic approach.

Example 3

Prostate Cancer

As described in more detail below, the results presented herein indicate that a panel of hypermethylation markers improves the sensitivity of histologic prostate cancer detection in sextant needle biopsies. In brief, fresh-frozen sextant biopsies were obtained from seventy-two excised prostates. A blinded histologic analysis was compared with QMSP molecular analysis for the ability of these techniques to sensitively and specifically detect the presence of prostate cancer. The quantitative real-time methylation-specific PCR analysed the hypermethylation of four genes: Tazarotene-induced gene 1 (TIG1), adenomatous polyposis coli (APC), retinoic acid receptor β2 (RARβ2), and glutathione S-transferaseπ=(GSTP1). Histological and QMSP results were compared with the final surgical pathological review of the resected prostates as the gold standard. This comparison found that histologic review alone detected carcinoma with a sensitivity of 64% (39 of 61 cases) and 100% specificity. Quantitative real-time methylation-specific PCR for TIG1, APC, RARβ2, and GSTP1 detected prostate carcinoma with a sensitivity of 70%, 79%, 89%, and 75%, respectively, with 100% specificity for all of the genes. Using this panel of methylation markers in combination with histology resulted in the detection of 59 of 61 (97%) cases of prostate with 100% specificity, a 33% improvement over histology alone.

The patients described in Harden et al., J Natl Cancer Inst, 95: 1634-7, 2003 were analysed using quantitative real-time methylation-specific PCR. Final surgical pathology revealed five occult prostate adenocarcinomas in five of sixteen cystoprostatectomy cases. The present study included sixty-one true prostate cancer cases and eleven true negative (nontumor) cases. The pathological stages and grades of the sixty-one cases are shown in Table 9 (below). A diagnosis of cancer was based on the requirement that only one of the six biopsies from each case needed to be called positive for the case to be positive.

TABLE 9

| Sample | Final surgical diagnosis (Gold standard) | Stage | PSA | Glenson score | T1G1 methylation | APC methylation | RARβ2 methylation | GSTP1 methylation | Blinded histology |
|---|---|---|---|---|---|---|---|---|---|
| 57366 | Ca | T3a | 4.6 | 347 | ■ | ■ | ■ | ■ | ■ |
| 57743 | Ca | T2 | 6.2 | 336 |  | ■ | ■ | ■ | ■ |
| 57933 | Ca | T3a | 5.9 | 347 | ■ | ■ | ■ | ■ | ■ |
| 58191 | Ca | T2 | 5.7 | 336 |  | ■ | ■ | ■ | ■ |
| 58213 | Ca | T2b | 5.8 | 336 |  | ■ | ■ | ■ | ■ |
| 58623 | Ca | T3a | 6.1 | 336 | ■ | ■ |  | ■ |  |
| 58911 | Ca | T2 | 4.6 | 347 |  | ■ | ■ | ■ | ■ |
| 59216 | Ca | T2 | 6.6 | 336 |  | ■ | ■ | ■ | ■ |
| 60255 | Ca | T2 | 4.4 | 336 |  |  | ■ | ■ | ■ |
| 60448 | Ca | T2b | 3.1 | 336 | ■ | ■ | ■ | ■ | ■ |
| 61514 | Ca | T3a | 4.0 | 347 | ■ | ■ | ■ | ■ | ■ |
| 61517 | Ca | T2 | 1.1 | 336 |  |  |  |  | ■ |
| 61745 | Ca | T2b | 6.1 | 336 | ■ | ■ | ■ | ■ | ■ |
| 61818 | Ca | T2b | 4.0 | 336 |  | ■ | ■ | ■ | ■ |
| 62551 | Ca | T2 | 7.1 | 336 | ■ | ■ | ■ | ■ | ■ |
| 63303 | Ca | T3b | 8.4 | unknown |  |  | ■ | ■ |  |
| 63498 | Ca | T2 | 8.2 | 336 |  |  | ■ | ■ |  |
| 64180 | Ca | T2 | 11.0 | 336 | ■ |  | ■ |  |  |
| 1311 | Ca | T2 | 2.9 | 336 |  |  | ■ |  |  |
| 1327 | Ca | T2 | 7.3 | 336 | ■ | ■ | ■ | ■ | ■ |
| 1806 | Ca | T2 | 6.7 | 336 | ■ | ■ | ■ | ■ | ■ |
| 2080 | Ca | T2 | 6.1 | 336 |  | ■ | ■ | ■ | ■ |
| 2219 | Ca | T2 | 0.8 | 336 |  | ■ | ■ |  | ■ |
| 2272 | Ca | T2 | 15.6 | 336 | ■ | ■ | ■ | ■ | ■ |
| 2308 | Ca | T3 | 4.7 | 336 | ■ | ■ | ■ | ■ | ■ |
| 2356 | Ca | T2 | 3.1 | 336 |  | ■ | ■ | ■ | ■ |
| 2667 | Ca | T3a | 10.3 | 347 | ■ | ■ | ■ | ■ | ■ |
| 3447 | Ca | T2 | 3.3 | 347 | ■ | ■ | ■ | ■ | ■ |
| 3498 | Ca | T2 | 0.5 | 336 |  | ■ | ■ |  |  |
| 4183 | Ca | T2 | 4.1 | 336 |  | ■ | ■ | ■ | ■ |
| 4446 | Ca | T3b | 6.1 | 347 | ■ | ■ | ■ | ■ | ■ |
| 4556 | Ca | T2 | 4.7 | 336 | ■ | ■ | ■ | ■ | ■ |
| 4758 | Ca | T2 | 1.3 | 336 |  |  | ■ |  |  |
| 4825 | Ca | T2 | unknown | 336 |  | ■ | ■ | ■ | ■ |
| 5565 | Ca | T2 | 3.1 | 336 | ■ | ■ | ■ | ■ | ■ |
| 5586 | Ca | T3 | 5.0 | 336 |  | ■ | ■ | ■ | ■ |
| 8564 | Ca | T2 | unknown | 347 | ■ | ■ | ■ | ■ | ■ |
| 25239 | Ca | unknown | 9.3 | 224 | ■ | ■ | ■ | ■ | ■ |
| 15487 | Ca | T2 | 3.5 | 347 | ■ | ■ | ■ | ■ | ■ |
| 16965 | Ca | T2 | 4.8 | 347 | ■ | ■ | ■ | ■ | ■ |
| 18242 | Ca | T2 | unknown | 336 | ■ | ■ | ■ | ■ | ■ |
| 18418 | Ca | T2 | 0.8 | 336 |  | ■ | ■ | ■ | ■ |
| 20145 | Ca | T2 | 9.5 | 336 | ■ | ■ | ■ | ■ | ■ |
| 20295 | Ca | T2 | 8.0 | 336 | ■ | ■ | ■ | ■ | ■ |
| 20418 | Ca | T2 | 5.3 | 347 | ■ | ■ | ■ | ■ | ■ |
| 20972 | Ca | T2 | 6.6 | 336 | ■ | ■ | ■ | ■ | ■ |
| 21619 | Ca | T2 | 5.0 | 336 | ■ | ■ | ■ | ■ | ■ |
| 21889 | Ca | T2 | 11.6 | 336 | ■ | ■ | ■ | ■ | ■ |
| 22316 | Ca | T2 | 5.2 | 347 | ■ | ■ | ■ | ■ | ■ |
| 22553 | Ca | T2 | 9.7 | 336 |  | ■ | ■ | ■ | ■ |
| 22650 | Ca | T2 | 5.0 | 336 |  | ■ | ■ | ■ | ■ |
| 24073 | Ca | T2 | 5.0 | 336 |  |  | ■ | ■ | ■ |
| 24076 | Ca | T2 | 5.0 | 336 | ■ | ■ | ■ | ■ | ■ |
| 24271 | Ca | T2 | 5.5 | 336 | ■ | ■ | ■ | ■ | ■ |
| 24309 | Ca | T2 | 7.3 | 336 |  | ■ | ■ | ■ | ■ |
| 24372 | Ca | T2 | 4.2 | 336 | ■ | ■ | ■ | ■ | ■ |
| 24431 | Ca | T2 | 25.8 | 336 | ■ | ■ | ■ | ■ | ■ |
| 24682 | Ca | T2 | 0.8 | 336 |  | ■ | ■ |  |  |
| 24697 | Ca | T2 | 7.8 | 336 | ■ | ■ | ■ |  |  |
| 24284 | Ca | T3a | 4.5 | 336 | ■ | ■ | ■ | ■ | ■ |
| 24825 | Ca | T3a | 4.2 | 336 | ■ | ■ | ■ | ■ | ■ |
| 2275 | NAD (BPH) |  |  |  |  |  |  |  |  |
| 3021 | NAD |  |  |  |  |  |  |  |  |
| 5664 | NAD |  |  |  |  |  |  |  |  |
| 6279 | NAD |  |  |  |  |  |  |  |  |
| 7213 | NAD |  |  |  |  |  |  |  |  |
| 7368 | NAD |  |  |  |  |  |  |  |  |
| 11600 | NAD |  |  |  |  |  |  |  |  |
| 11738 | NAD (PIN) |  |  |  |  |  |  |  |  |
| 17903 | NAD |  |  |  |  |  |  |  |  |
| 20973 | NAD (PIN) |  |  |  |  |  |  |  |  |
| 22325 | NAD (PIN) |  |  |  |  |  |  |  |  |

Abbreviations:
Ca, prostate adenocarcinoma;
NAD, no abnormality detected (nontumor tissue);
BPH, benign prostatic hyperplasia;
PIN, prostatic intraepithelial neoplasia;
PSA, prostate-specific antigen (ng/ml).

*Filled boxes indicate positive assay (cancer) and open boxes indicate negative assay (nontumor) based on the designated cutoff value (methylation) or morphology.

Figure 10:
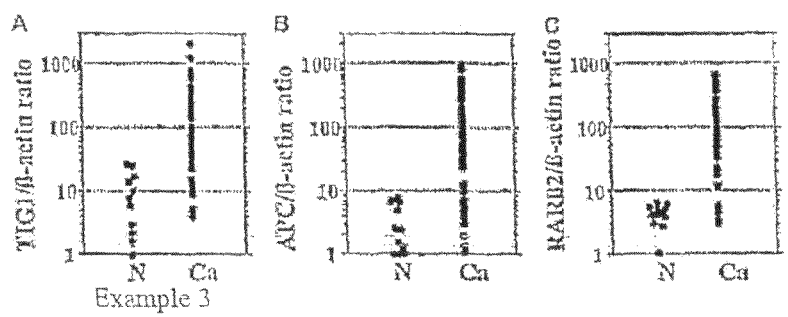
FIGS. 10A-C are scatter plots showing quantitative real-time methylation-specific PCR for TIG1 (A), APC (B), and RARβ2 (C) in nontumor samples (N) and prostate adenocarcinoma (Ca). Measurements are expressed as a methylation ratio, defined as the ratio of the fluorescence intensity values for each gene to that of β-actin, multiplied by 1000. Quantitative real-time methylation-specific PCR revealed a significant difference in the ratio between the cancer and nontumor group in TIG1, APC, and RARβ2 (P<0.0001).
Figure 11:
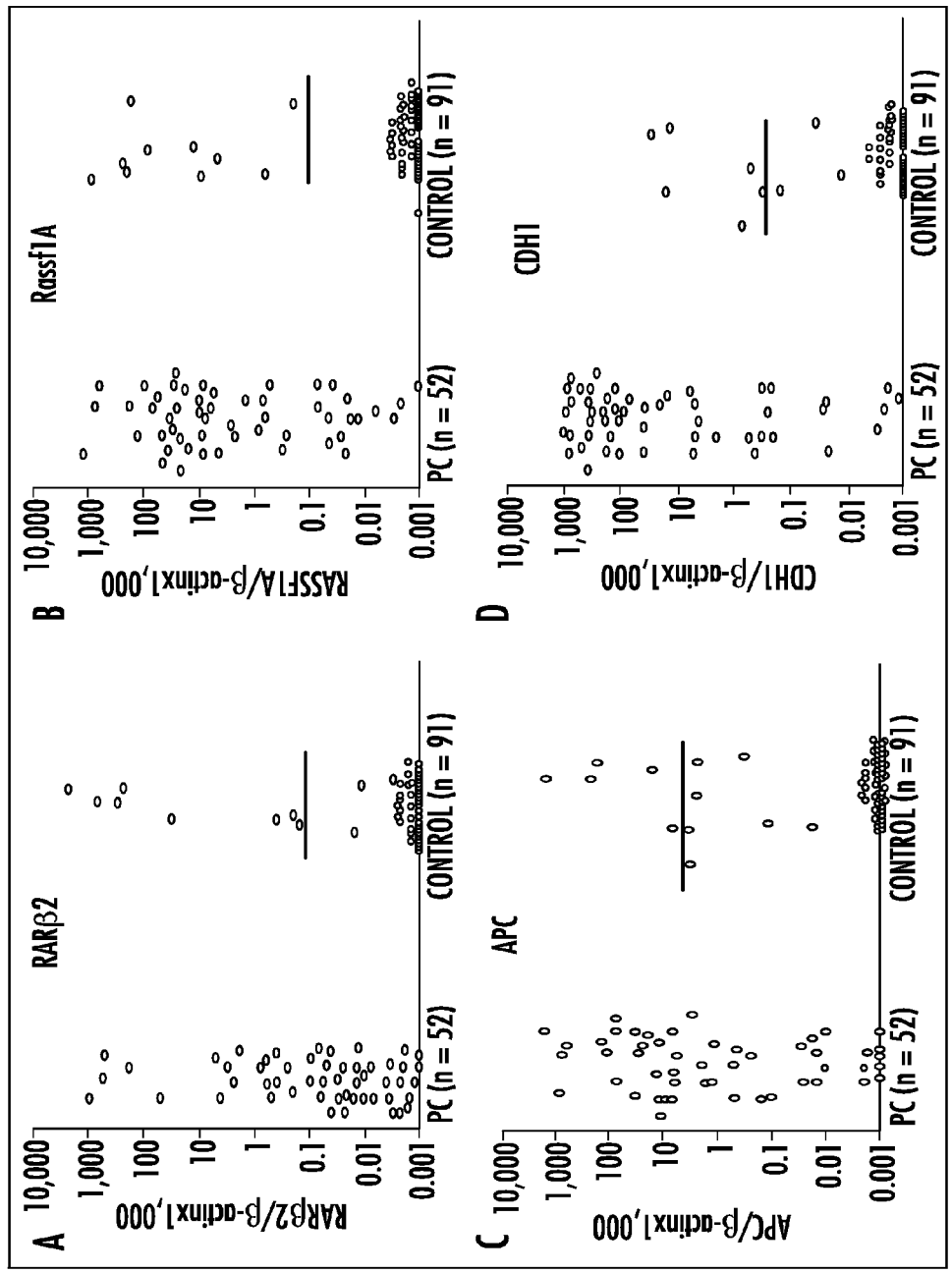
FIGS. 11A-D are scatter plots showing representative examples of quantitative methylation-specific polymerase chain reaction (PCR) methylation levels of Rassf1A, RARβ2, APC, and CDH1 in urine sediment DNA of prostate cancer patients (PC; n=52) and nongenitourinary cancer individuals (controls; n=91). Calculation of the gene of interest/actin ratios was based on the fluorescence emission intensity values for both the gene of interest and actin obtained by quantitative real-time PCR analysis. The relative amount of methylated promoter DNA was much higher in urine sediment from PC patients compared with controls. Black bar denotes the calculated cutoff value. Values designated as 0.001 are zero values, which can not be plotted correctly on a log scale.

First a pilot study was performed to determine specific analytical thresholds for TIG1, APC, and RARβ2 methylation. The methylation status of one hundred twenty-one primary prostate cancer and twenty-nine benign prostatic hyperplasia samples was assayed and established the threshold for each gene that most efficiently distinguished cancer and benign prostatic hyperplasia samples. The biopsy samples were then prospectively examined using this threshold in a blinded fashion. TIG1 quantitative real-time methylation-specific PCR detected prostate carcinoma with a sensitivity of 70% (43 of 61) and 100% specificity (11 of 11). This was a 6% improvement compared with histology alone (Table 9). Representative results of quantitative real-time methylation-specific PCR for TIG1 are shown in FIG. 9. APC and RARβ2 quantitative real-time methylation-specific PCR showed 79% and 89% sensitivity with 100% specificity (Table 9), representing 15% and 25% improvements respectively over blinded histologic examination. FIGS. 10A-C showed the highest methylation ratio in the sextant biopsies from each of the cases. The methylation ratio of all three of the genes (TIG1, APC, and RARβ2) revealed a significant difference between the cancer and nontumor groups (P<0.0001).

To optimize the highest sensitivity of quantitative real-time methylation-specific PCR in diagnosis of prostate cancer, a variety of combinations was checked with these methylated genes. As shown in Table 10, the combination of TIG1 and RARβ2 showed the highest sensitivity of 95% (58 of 61) with 100% specificity, representing a 31% improvement compared with histology alone.

TABLE 10

Sensitivity of histological assessment and quantitative real-time methylation-specific PCR for TIG1, APC, RARβ2, and GSTP1

| Assay | Detection sensitivity | |
|---|---|---|
| | Cancer | Normal |
| Blinded histological assessment | 39/61 (64%) | 0/11 (0%) |
| Methylation of one gene* | | |
| TIG1 | 43/61 (70%) | 0/11 (0%) |
| APC | 48/61 (79%) | 0/11 (0%) |
| RARβ2 | 54/61 (89%) | 0/11 (0%) |
| GSTP1† | 46/61 (75%) | 0/11 (0%) |
| Methylation + histology | | |
| TIG1 + histology | 50/61 (82%) | 0/11 (0%) |
| APC + histology | 52/61 (85%) | 0/11 (0%) |
| RARβ2 + histology | 56/61 (92%) | 0/11 (0%) |
| GSTP1 + histology† | 48/61 (79%) | 0/11 (0%) |
| Combination of methylated genes | | |
| GSTP1 + TIG1 | 54/61 (89%) | 0/11 (0%) |
| GSTP1 + APC | 52/61 (85%) | 0/11 (0%) |
| GSTP1 + RAR β2 | 55/61 (90%) | 0/11 (0%) |
| GSTP1 + TIG1 + APC + RARβ2 | 59/61 (97%) | 0/11 (0%) |

*By quantitative real-time methylation-specific PCR.
†Data from Harden et al supra.

Furthermore, using all four of the methylation markers, 97% of prostate cancers were detected, representing a 33% improvement in sensitivity compared with histology alone. Using the combination, detected fifty-nine of sixty-one cancers. All of the benign samples were correctly identified as negative (Table 10).

The preferred method for definitive diagnosis of prostate cancer is histologic analysis of sextant biopsies. Prostate needle biopsies provide not only histologic diagnosis, but also additional information that is critical for the management of prostate cancer patients (Epstein et al., J Urol, 166: 402-10, 2001). Diagnosis of prostate cancer by biopsy can be difficult for small moderate-grade cancers (Epstein et al., Hum Pathol, 26(2): 223-9, 1995). Needle biopsies contain only small samples of tissue and often include only a few malignant glands among many benign glands. Thus, it is not uncommon for many patients to be subjected to multiple biopsy examinations before a correct diagnosis is established. In this study, the ability of a methylation panel to improve the sensitivity of standard histology for prostate cancer detection in needle biopsies was tested. Using a combination of four genes, TIG1, APC, RARβ2, and GSTP1, there was an improvement in sensitivity. In fact, 95% of prostate carcinomas were identified with perfect specificity (Table 10). A combination of all of the methylation markers identified herein demonstrated 97% sensitivity. Nevertheless, two cases of prostate carcinoma were missed. These two missed cases harbored extremely small tumors, suggesting sampling error in the needle biopsies.

Histologic review of frozen sections is technically more difficult than paraffin sections. This might partially explain the twenty-two cases of prostate carcinoma that were missed by histologic analysis. A significant number of prostate cancers is routinely missed at initial biopsy even using paraffin sections (Epstein supra). High specificity is important for any diagnostic test because an established cancer diagnosis leads to major surgery and/or radical treatments with associated toxicities and side effects. The cost of quantitative real-time methylation-specific PCR assays is comparable with routine histologic assessment.

Adding gene methylation testing to routine histologic examination for the diagnosis of prostate cancer. Quantitative real-time methylation-specific PCR assays of key prostate cancer genes should be incorporated into larger diagnostic trials aimed at early disease detection. Validation of these assays in definitive studies could change the standard evaluation of sextant biopsies after routine prostate-specific antigen screening.

Example 4

Prostate Carcinoma

Urine sediment DNA was assayed for aberrant methylation of nine gene promoters (p16INK4a, p14$^{ARF}$, MGMT, GSTP1, RARβ2, CDH1 [E-cadherin], TIMP3, Rassf1A, and APC) from fifty-two patients with prostate cancer and twenty-one matched primary tumors by quantitative fluorogenic real-time polymerase chain reaction. Urine sediments from 91 age-matched individuals without any history of genitourinary malignancy were also analyzed as controls. As reported herein, promoter hypermethylation of at least one of the genes studied was detected in urine samples from all fifty-two prostate cancer patients. Urine samples from the ninety-one controls without evidence of genitourinary cancer revealed no methylation of the p16, ARF, MGMT, and GSTP1 gene promoters, whereas methylation of RARβ2, TIMP3, CDH1, Rassf1A, and APC was detected at low levels. Overall, methylation found in urine samples matched the methylation status in the primary tumor. A combination of only four genes (p16, ARF, MGMT, and GSTP1) would theoretically allowed detection of 87% of prostate cancers with 100% specificity. These data indicate the utility of the noninvasive QMSP assay in urine DNA for early detection and surveillance of prostate cancer.

The demographic and clinical characteristics of cancer patients included in this study are listed in Table 11.

TABLE 11

Clinical Characteristics of Cancer Patients

| Characteristic | No. of Patients (N = 52) |
|---|---|
| Age, years | |
| Median | 59 |
| Range | 39-81 |
| Stage | |
| T2 | 24 |
| T3a | 18 |
| T3b | 10 |
| Gleason score | |
| 4-5 | 2 |
| 6 | 22 |
| 7 | 19 |
| 8 | 3 |
| 9-10 | 6 |
| Preoperative serum PSA | |
| ≤4 ng/mL | 7 |
| 4-8 ng/mL | 21 |
| 8.1-12 ng/mL | 10 |
| >12 ng/mL | 14 |

Abbreviation: PSA, prostate-specific antigen.

Methylation levels of selected genes in urine sediment of prostate cancer patients and control urine sediments are shown in FIGS. 11A-11D. Aberrant promoter hypermethylation of at least one of the genes investigated was detected in the urine sediment of all the 52 prostate cancer patients (100%), and 42 of these urine DNA samples (80%) were positive for at least three genes simultaneously. Moreover, 87% of the samples from patients with prostate cancer demonstrated methylation in at least one of the four genes (p16, ARF, MGMT, and GSTP1) with 100% specificity (i.e., all of the 91 control samples were negative for methylation in these four genes). The frequency and median methylation values (gene/β-actin×1,000) for each gene in urine DNAs are listed in Table 12. Methylation positive urine samples from prostate cancer patients ranged from 19% in MGMT to 77% in CDH1 (Table 12).

On the basis of 66 male controls, sensitivity and specificity were calculated and are detailed in Supplementary Table 1. Interestingly, most of the methylation-positive controls came from patients with benign prostate hyperplasia.

Figure 12:
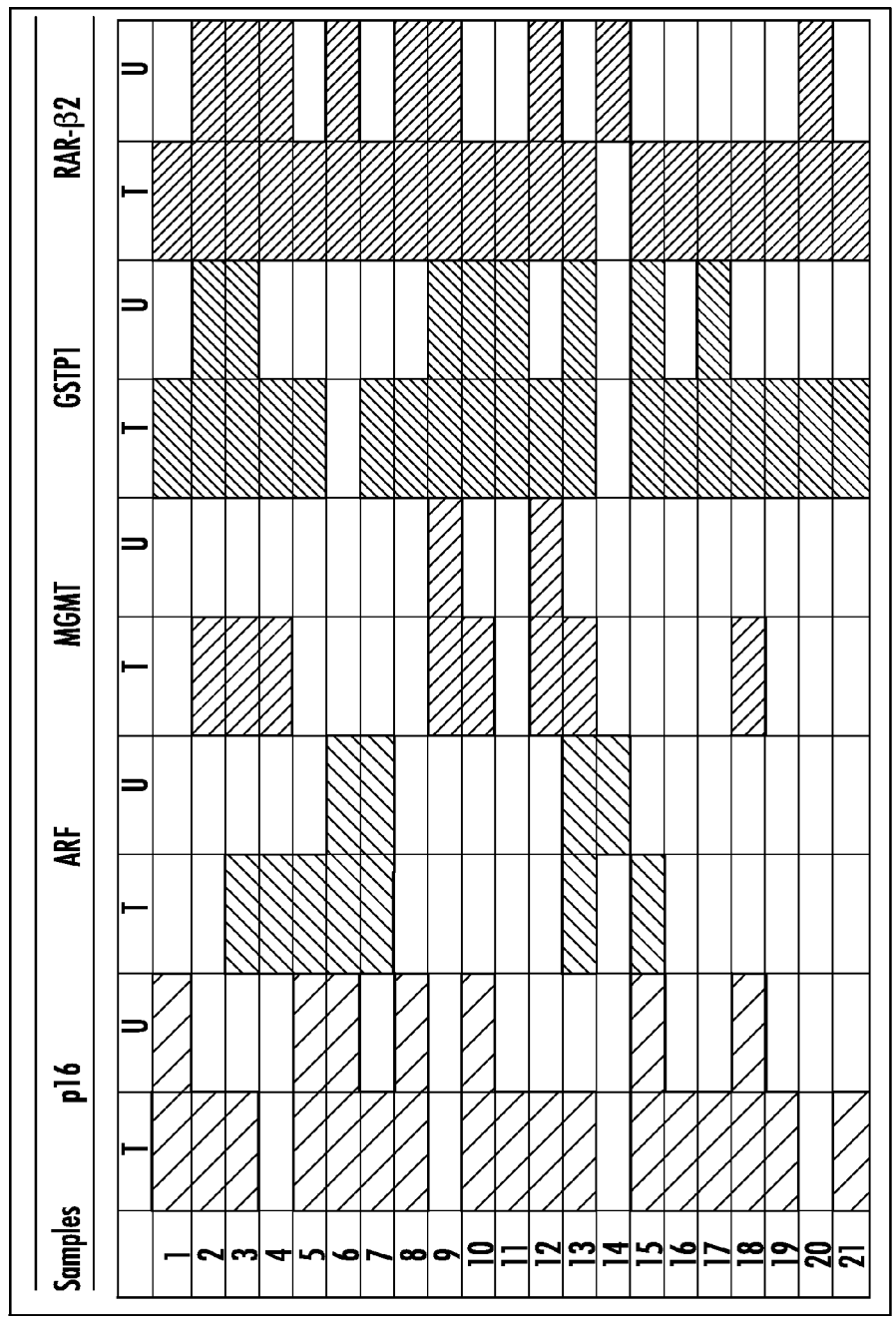
FIG. 12 shows a summary of p16, ARF, MGMT, GSTP1, and RARβ2 methylation in twenty-one corresponding tissue (T) and urine sediment (U) samples. Shaded boxes represent samples that are methylated; white boxes represent samples devoid of methylation.

To confirm whether the epigenetic alterations in urine sediments were identical to the matched tumors, five genes (p16, ARF, MGMT, GSTP1, and RARβ2) were analyzed in twenty-one paired primary tumor samples. The methylation patterns of these five genes in primary tumor and matched urine DNA are shown in FIG. 12. The five genes were selected because of absence or near absence of methylation in normal prostate tissue (Jeronimo et al., Clin Cancer Res 10:8472-8478, 2004). Twenty-one matched available primary prostate cancer samples were analysed. The DNA was extracted from a high Gleason score area Overall, identical methylation patterns were found in the urine and corresponding tumor DNA. Aberrant methylation was detected in only one urine DNA sample of a prostate cancer patient without methylation in the corresponding tumor (sample No. 14, FIG. 12). In this patient methylation of ARF and RARβ2 was found only in the urine sample. This urine sample may contain tumor cells from an area separate from where the tissue DNA was extracted. The analytic sensitivity of these five genes is shown in FIG. 12.

The development of real-time PCR has simplified the study of genes inactivated by promoter hypermethylation in human cancer. It is a highly sensitive assay that is capable of detecting methylated alleles in the presence of a more than 1,000-fold excess of unmethylated alleles. Yet, it is more stringent and more specific because, in addition to the two PCR primers, the fluorescent-labeled hybridization probe has to anneal correctly between the two primers. QMSP is often more sensitive than conventional MSP. Results may vary depending on the promoter, primers, and condition. Others have found a higher frequency of APC methylation by QMSP compared with conventional MSP in cell lines (Virmani et al., Cancer Epidemiol Biomarkers Prev 11:291-297, 2002). In general, the methylation frequency in primary tumors of each tested gene was higher than previous reports because of the use of QMSP or our selective dissection of a higher Gleason score area for DNA extraction.

TABLE 12

Frequency of Aberrant Methylation in Urine Sediments

| Genes | Cancer Patients With Methylation Positive Urine (n = 52) | | Controls With Methylation Positive Urine (n = 91) | | P | In Cancer Patients | | Cutoff |
|---|---|---|---|---|---|---|---|---|
| | No. | % | No. | % | | Median | Range | |
| APC | 25 | 48 | 4 | 4 | <.0001 | 2.53 | 0-1,842.41 | 4.5 |
| ARF* | 19 | 37 | 0 | 0 | <.0001 | 0 | 0-1,430 | 0 |
| CDH1 | 40 | 77 | 5 | 6 | <.0001 | 76.66 | 0-1,000 | 0.3 |
| GSTP1* | 25 | 48 | 0 | 0 | <.0001 | 0 | 0-210 | 0 |
| MGMT | 10 | 19 | 0 | 0 | <.0001 | 0 | 0-619 | 0 |
| p16* | 19 | 37 | 0 | 0 | <.0001 | 0 | 0-982 | 0 |
| RAR-β2* | 18 | 35 | 8 | 9 | <.0001 | 0.05 | 0-963.78 | 0.1 |
| Rassf1A* | 38 | 73 | 10 | 11 | <.0001 | 7.82 | 0-1,087.59 | 0.1 |
| TIMP3* | 19 | 37 | 8 | 9 | <.0001 | 0 | 0-202 | 1 |

NOTE.
At least one of the genes investigated was detected in the urine sediment of all the 52 prostate cancer patients (100% diagnostic coverage).
*At least one of the genes (ARF, GSTP1, MGMT, and p16) investigated was detected in 87% of the samples with 100% specificity.

Aberrant methylation in the urine sediment of primary prostate carcinoma had no significant level of correlation with patient demographic data, including age, histologic subtype, and staging of the tumor (data not shown). Others have found a significant correlation between methylation and Gleason score, preoperative serum PSA, and tumor stage (Maruyama et al., Clin Cancer Res 8:514-519, 2002). The reason behind these discrepancies may be the indirect measurement of methylation in urine instead of primary tumor DNA and the different clinical subgroups represented in various studies (Table 13).

Two metastatic suppressor genes, CDH1 and TIMP3, were frequently methylated in the urine sediment of prostate cancer patients (77% and 37%, respectively). CDH1 methylation finding is similar with results obtained in studies using conventional MSP in primary prostate tumors (Li et al., J Urol 166: 705-709, 2001; Kallakury et al., Cancer 92:2786-2795, 2001), which reported that the severity of CDH1 methylation correlated with tumor progression. In the present study, no correlation between CDH1 methylation and tumor grade and stage was observed. Despite establishing a cutoff value (Table 13) in our controls, low levels of CDH1 methylation were

TABLE 13

Methylation of Individual Markers and Clinical Parameters-in Urine DNA From Cancer Patients

| Parameter | No. of Patients | CDH1 | APC | RASSF1A | GSTP1 | p16 | MGMT | RAR-β2 | ARF | TIMP3 |
|---|---|---|---|---|---|---|---|---|---|---|
| Preoperative serum PSA | | | | | | | | | | |
| ≤4 ng/mL | 7 | 6 | 4 | 6 | 3 | 4 | 1 | 3 | 2 | 1 |
| 4-8 ng/mL | 21 | 19 | 13 | 18 | 9 | 7 | 7 | 8 | 7 | 10 |
| 8.1-12 ng/mL | 10 | 10 | 5 | 7 | 6 | 6 | 1 | 2 | 2 | 6 |
| >12 ng/mL | 14 | 5 | 3 | 7 | 7 | 3 | 0 | 5 | 6 | 2 |
| Gleason score | | | | | | | | | | |
| 4-5 | 2 | 2 | 1 | 2 | 2 | 1 | 1 | 1 | 2 | 1 |
| 6 | 22 | 20 | 14 | 16 | 11 | 9 | 6 | 10 | 7 | 11 |
| 7 | 19 | 14 | 5 | 14 | 7 | 7 | 2 | 5 | 4 | 5 |
| 8 | 3 | 2 | 2 | 3 | 1 | 1 | 0 | 1 | 1 | 1 |
| 9-10 | 6 | 2 | 3 | 3 | 4 | 2 | 0 | 1 | 3 | 1 |
| Stage | | | | | | | | | | |
| T2 | 24 | 16 | 11 | 20 | 12 | 10 | 5 | 7 | 9 | 7 |
| T3a | 18 | 15 | 9 | 14 | 10 | 8 | 4 | 9 | 5 | 10 |
| T3b | 10 | 9 | 5 | 4 | 3 | 2 | 0 | 2 | 3 | 2 |

Abbreviation: PSA, prostate-specific antigen.
Methylation positive indicates level above the empiric cutoff determined by comparing patients with controls and maximizing likelihood ratio positive.

Two reported methylated DNA repair genes (GSTP1 and MGMT) were investigated; These genes are commonly found in various tumor types including prostate cancer. Using conventional MSP, methylated GSTP1 alleles were detected in the urine sediment from 27% of the patients with a methylated primary tumor (Cairns et al., Clin Cancer Res 7:2727-2730, 2001). In the present study, GSTP1 was methylated in 48% of urine sediment samples. The reason for this discrepancy may be the primer design, but it should be noted that the sample size was different in both studies and that tumor stages and grade also differed. For prostate cancer, there was no case in which a urine sediment DNA sample gave a positive GSTP1 methylation result in the absence of methylation in the corresponding tumor (Cairns supra; Goessl et al., Cancer Res 60:5941-5945, 2000). MGMT methylation was found in 19% of urine sediment samples compared with less than 25% of primary prostate tumors by conventional MSP (Maruyama et al., Clin Cancer Res 8:514-519, 2002; Goessl supra; Konishi et al., Japan J Cancer Res 93:767-773, 2002).

Three cell cycle regulators p16, ARF, and possibly Rassf1A) were included in our study. Previous reports of methylation in primary tumor tissues and prostate cancer cell lines ranged from 3% to 69% for p16 methylation (Maruyama supra; Konishi supra; Yamanaka et al., Int J Cancer 106: 382-387, 2003; Konishi et al., Am J Pathol 160:1207-1214, 2002; Herman et al., Cancer Res 55:4525-4530, 1995; Jarrard et al., Genes Chromosomes Cancer 19:90-96, 1997) 6% for ARF methylation and 53% to 100% for Rassf1A methylation. These discrepancies may be a result of differences in the methylation assays used and the inclusion of tumors with different stages and grades.

found in five (6%) of 91 samples from individuals without any known genitourinary malignancy. TIMP3 is the third member of the TIMP family of proteins and is believed to play a significant role in controlling extracellular matrix remodeling. TIMP3 was found to be methylated in 24% to 28% of various human cancers (Kang et al., Lab Invest 83:635-641, 2003; Alonso et al., Cancer Genet Cytogenet 144:134-142, 2003; Schagdarsurengin et al., Oncogene 22:1866-1871, 2003).

TIMP3 methylation was found in 37% of urine sediments from prostate cancer patients. The use of retinoids to suppress tumor development has been evaluated in several animal models of carcinogenesis, including models of skin, breast, oral cavity, lung, hepatic, GI, prostatic, and bladder cancer (Evans et al., Br J Cancer 80:1-8, 1999). Retinoids act primarily via nuclear receptors encoded by the RARβ gene. Because the isoforms RARβ2 and RARβ4 are frequently methylated in other cancers (Widschwendter et al., J Natl Cancer Inst 92:826-832, 2000; Yang et al., Am J Pathol 158: 299-303, 2001; Ivanova et al., BMC Cancer 2:4, 2002. The methylation of the RARβ2 promoter in urine sediment DNA was also investigated. RARβ2 was methylated in 53% to 95% of primary prostate tumor tissues.

The APC protein is an integral part of the wnt-signaling mechanism, but it also plays a role in cell-cell adhesion, stability of the microtubular cytoskeleton, cell cycle regulation, and possibly apoptosis. The promoter regions of APC gene were aberrantly methylated in many types of cancer. In other studies, APC was found to be hypermethylated in 27% to 95% of primary prostate tumors (Jeronima supra;

Maruyama supra) compared with 54% methylation in urine sediment DNA reported in the present study.

There have been few studies (Cairns supra; Goessl supra) using an extended panel of methylation markers for the detection of prostate cancer in urine sediment. Thus, the methylation assay using nine different genes in the urine DNA extends previous observations. The high sensitivity (87%) using just four genes (p16, ARF, MGMT, and GSTP1) with undetectable methylation levels in all control samples (Table 12) indicates that detection of tumor molecular signatures in body fluids is useful for the identification of high-risk patients and patients with preinvasive or early-stage lesions as well as for monitoring residual disease. Molecular approaches characterized by high specificity have variable sensitivity, perhaps because of the presence of low tumor DNA quantities in urine or the high level of contamination with normal DNA. Several approaches to improve assay sensitivity have been applied to clinical samples. Sensitivity has been improved over conventional MSP by performing a semi-nested MSP after a DNA preamplification step (Kersting et al., J Clin Oncol 18:3221-3229, 2000) or a nested two-stage PCR (Palmisano et al., Cancer Res 60:5954-5958, 2000) usually with decreased specificity for clinically definable disease. The sensitivity of QMSP in urine sediment could be further increased by isolating the aberrant cells from urine before DNA extraction or increasing the number of prostate cancer-specific markers.

Exfoliative material (present in urine, stool, sputum, bronchoalveolar lavage, bronchial brushings, and so on) offers diagnostic possibilities. The sensitivity of current cytologic tests is low and virtually of limited utility for prostate cancer detection. Diagnostic tools, such as QMSP, that are based on DNA alterations provide high specificity and sensitivity are of enormous benefit to patients, particularly because such specimens are obtained using noninvasive means. Accordingly, the detection of aberrant methylation in urine DNA offers a desirable approach for the noninvasive diagnosis of prostate cancer. Apart from prostate cancer detection, the detection of aberrant methylation in the urine can be used to monitor disease after curative surgery. If methylated DNA disappears shortly in urine after curative surgery, the reappearance of these markers may suggest recurrence of disease that may require more intensive screening and aggressive treatment.

Desirably, this simple and noninvasive method for detecting prostate cancer is readily automated and has many potential clinical applications, including primary diagnosis, monitoring for relapse, and measurement of therapeutic response. This study was performed on patients referred after PSA screening or other clinical suspicion. Additional studies are necessary to elucidate the role of detecting aberrant methylation in urine as a tool for early detection and surveillance of prostate cancer either alone or in combination with serum PSA or digital rectal examinations. Moreover, other cancers, including bladder and kidney cancer, contribute cellular DNA to urine sediment. Thus, a panel of carefully selected methylation markers in urine sediment could be envisioned that both detects and then discriminates among a variety of urologic tumors.

The results reported herein were obtained using the following methods and materials.

Example 1

Bladder Cancer Sample Collection

Tissue samples and matched urine sediment were evaluated for fifteen patients with bladder cancer. Each of the patients underwent curative surgery at the Johns Hopkins University, School of Medicine. Tissue specimens were immediately snap frozen in liquid nitrogen and stored at −80° C. Hemotoxylin and eosin (H&E)-stained sections were histologically examined every 20 sections for the presence or absence of tumor cells, as well as for tumor density. Only sections that showed more than 70% tumor cells were used for DNA extraction.

Additionally the urine sediment of 160 patients with bladder cancer was examined (total=175) (pTa, pTis, n=48; pT1, n=26; pT2≥n=101). Detailed information for these patients is summarized in Table 1. Fifty milliliters of voided urine was collected prior to surgical intervention. The Institutional Review Board of the Johns Hopkins Hospital approved the study. Urine samples from ninety-four age-matched [Median 58.5 years (range 28 to 84 years)] individuals without a history of genitourinary malignancy were used as controls. Of these ninety-four cases, nine patients were diagnosed as Benign Prostate Hyperplasia (BPH), ten cases harbored atypical cells by urine cytology examination, and five cases had primary cancers in other sites (1 Non-small cell carcinoma of Lung, 1 Basal Cell Carcinoma of Skin, 1 Malignant Melanoma of Leg, 1 Kaposi's Sarcoma of the Leg and 1 Infiltrating Ductal Carcinoma of the Breast), 1 fibroepithelial polyp of the bladder, 3 tubular adenoma of the colon, 1 case of organizing thrombus of the vagina, 1 neurogenic bladder, 2 bladder papilloma, 20 cases with either macroscopic or microscopic hematuria, 42 cases seen for vague urological symptoms without malignancy. Among the ninety-four cases, sixty-eight were male and twenty-six were female. Absence of genitourinary neoplasm in the controls was confirmed by complete evaluation including cystoscopy. Fifty milliliters of voided urine was collected from all controls and cases prior to definite surgery.

Urine samples were spun at 3000×g for 10 minutes to pellet urinary sediment. The pellet was subsequently washed twice with phosphate-buffered saline. All samples were stored at −80° C. Approval for research on human subjects was obtained from the Johns Hopkins University Institutional Review Boards.

Example 1

DNA Extraction

Frozen urine cell pellet and microdisected tissues were digested with 1% SDS and 50 µg/ml proteinase K (Boehringer Mannheim, Germany) at 48° C. overnight, followed by phenol/chloroform extraction and ethanol precipitation of DNA as previously described (Hoque et al., Cancer Res 2003; 63:2216-22).

Example 1

Bladder Cancer Bisulfite Treatment

DNA from primary tumor and urine sediment was subjected to bisulfite treatment, as described previously with little modification (Herman et al., Proc Natl Acad Sci USA 1996; 93:9821-6). Briefly, 2 µg of genomic DNA was denatured in 0.2 M NaOH for 20 minutes at 50° C. The denatured DNA was diluted in 500 µl of freshly prepared solution of 10 mM hydroquinone and 3 M sodium bisulfite, and incubated for 3 hours at 70° C. After incubation, the DNA sample was desalted through a column (Wizard DNA Clean-Up System, Promega), treated with 0.3 M NaOH for 10 minutes at room temperature, and precipitated with ethanol. The bisulfite-modified genomic DNA was resuspended in 120 μl of LoTE (2.5 mM EDTA, 10 mM Tris-HCL) and stored at −80° C.

Example 1

Bladder Cancer Methylation Analysis

Templates were amplified by a fluorescence based-real-time PCR as previously described (Harden et al., Clin Cancer Res 2003; 9:1370-5). In brief, primers and probes were designed to specifically amplify the bisulfite-converted promoter of the gene of interest and details in Table 14 (SEQ ID Nos: 1-30).

1000). Fluorogenic PCRs were carried out in triplicate in a reaction volume of 20 μl consisting of 600 nM of each primer, 200 nM of probe, 5 units of Taq Polymerase, 200 μM each of dATP, dCTP, and dGTP; 400 of μM dTTP; and 5.5 mM MgCl$_2$. Three microliters of treated DNA solution was used in each real-time MSP reaction. Amplifications was carried out in 384-well plates in a 7900 Sequence detector (Perkin-Elmer Applied Biosystems). Each plate consisted of patient samples and multiple water blanks, as well as positive and negative controls. Leukocytes from a healthy individual were methylated in vitro with excess SssI methyltransferase (New

TABLE 14

| Gene | Forward 5'-3' (SEQ ID Nos: 1-10) | Probe 6FAM 5'-3'TAMRA (SEQ ID Nos: 11-20) | Reverse 5'-3' (SEQ ID Nos: 21-30) | Genbank# | Amplicon size (Nucleotide range) | Annealing Temperature |
|---|---|---|---|---|---|---|
| ACTB | TGG TGA TGG AGG AGG TTT AGT AAG T (390-414) | ACC ACC ACC CAA CAC ACA ATA ACA AAC ACA (432-461) | AAC CAA TAA AAC CTA CTC CTC CCT AAA (496-522) | Y00474 | 133 bp; (390-522) | 60 |
| APC | GAA CCA AAA CGC TCC CCA T (761-779) | CCC GTC GAA AAC CCG CCG ATT (781-802) | TTA TAT GTC GGT TAC GTG CGT TTA TAT (808-834) | U02509 | 74 bp; (761-834) | 60 |
| ARF | ACGGGCGTTTTCGGTA GTT (5447-5465) | CGACTCTAAACCCTACGCA CGCGAAA (5468-5498) | CCGAACCTCCAAAATCTCG A (5496-5515) | AF082338 | 68 bp; (5447-5515) | 60 |
| CDH1 | AATTTTAGGTTAGAGGG TTATCGCGT (842-867) | CGCCCACCCGACCTCGCAT (870-888) | TCCCCAAAACGAAACTAAC GAC (890-911) | L34545 | 69 bp; (842-911) | 60 |
| GSTP1 | AGT TGC GCG GCG ATT TC (1033-1049) | CGG TCG ACG TTC GGG GTG TAG CG (1073-1095) | GCC CCA ATA CTA AAT CAC GAC G (1151-1172) | M24485 | 140 bp; (1033-1172) | 60 |
| MGMT | CGA ATA TAC TAA AAC AAC CCG CG (1029-1051) | AAT CCT CGC GAT ACG CAC CGT TTA CG (1084-1109) | GTA TTT TTT CGG GAG CGA GGC (1130-1150) | X61657 | 122 bp; (1029-1150) | 60 |
| P16 | TTA TTA GAG GGT GGG GCG GAT CGC (25-48) | AGT AGT ATG GAG TCG GCG GCG GG (99-121) | GAC CCC GAA CCG CGA CCG TAA (154-174) | U12818 | 150 bp; (25-174) | 60 |
| RAR-β2 | GGGATTAGAATTTTTAT GCGAGTTGT (907-934) | TGTCGAGAACGCGAGCGAT TCG (948-969) | TACCCCGACGATACCCAAAC (980-999) | X56849 | 93 bp; (907-999) | 60 |
| Rassf1A | GCG TTG AAG TCG GGG TTC (45-62) | ACA AAC GCG AAC CGA ACG AAA CCA (69-92) | CCC GTA CTT CGC TAA CTT TAA ACG (96-119) | NM 007182 | 75 bp; (45-119) | 60 |
| TIMP3 | GCGTCGGAGGTTAAGGTT GTT (1051-1072) | AACTCGCTCGCCCGCCGAA (1081-1099) | CTCTCCAAAATTACCGTACG CG (1122-1143) | U33110 | 93 bp; (1051-1143) | 62 |

The ratios between the values of the gene of interest and the internal reference gene, β-actin, obtained by Taqman analysis were used as a measure for representing the relative level of methylation in the particular sample (Target gene/β-actin×

England Biolabs Inc., Beverly, Mass.) to generate completely methylated DNA and serial dilutions of this DNA were used for constructing the calibration curves on each plate. A summary of all the nine genes examined is described in Table 15.

TABLE 15

| Gene symbol | loci | Name | Tumors with hypermethylation | Proposed function |
|---|---|---|---|---|
| APC | 5q14 | Adenomatous polyposis coli | Colon, Lung | WNT signaling pathway; Beta-catenin degradation, tumor suppressor |
| ARF | 9P21 | p14 | Colon, lymphoma | Cell cycle regulator, tumor suppressor |
| CDH1 | 16q22.1 | E-cadherin | AML, bladder, breast, colon, gastric, thyroid | Cell adhesion |

TABLE 15-continued

| Gene symbol | loci | Name | Tumors with hypermethylation | Proposed function |
|---|---|---|---|---|
| CDKN2A | 9P21 | p16 | AML, bladder, colon, gastric, lymphoma, melanoma | Cell cycle regulator, tumor suppressor |
| GSTPI | 11q13 | Glutathione S-transferaseXX | Breast, prostate, hepatocellular | Protect against oxidant and electrophilic carcinogens |
| HIC1 | 17p13.3 | Hypermethylated in cancer | Brain, breast, colon, renal, leukemia, Lymphoma | Zinc finger transcription factor; potential tumor suppressor |
| MGMT | 10q | o6-methylguanine-DNA methyltransferase | Brain, colon, lymphoma, non-small cell lung cancer | DNA repair |
| RassflA | 3p21.3 | | lung, breast, overy, kidney, thyroid | Block cell cycle progression |
| RAR-beta | 3p24 | | breast, cervix | Cell cycle arrest and growth inhibition |
| TIMP3 | 22q | Tissue inhibitor of metallo-proteinase | Brain, breast, colon, kidney, lung, pancreatic | Suppresses metastasis, angiogenesis and tumor growth |

Example 1

Bladder Cancer Statistical Analysis

The major statistical endpoint in this study was the quantitative methylation levels for each gene in cancer cases and in controls. From these levels, receiver operating characteristic (ROC) curves were constructed for each of nine genes for the detection of bladder cancer. The value of using a binary cutoff (zero methylation) versus the quantitative level was also explored, via multivariate logistic models. Since four of the genes showed 100% specificity, a two step decision rule was constructed. In the first step, four genes with 100% specificity were used to identify an initial group of cancers. Among the patients in whom none of these genes were methylated, a logistic regression (Cox, D. R. The Analysis of Binary Data. London: Methuen, 1970) utilizing the remaining genes was performed. ROC curves were produced by combining sensitivity and 100% specificity achieved from the first step with the logistic regression results from the second step. Internal validation of the logistic regression models was done using an approximation to the leave one out jackknife procedure provided by the SAS classification table option (SAS Institute Inc. SAS/STAT User=s Guide (Volume 2): Statistics, Version 8 Edition. Cary, N.C.: SAS Institute Inc., 1999). All multivariate procedures were preceded with univariate analyses. As an exploratory tool, a Bayesian network algorithm was also applied, which allowed for the dichotomization of every gene at a methylation level that maximized discrimination between cases and noncases, and unrestricted non-parametric combination of binary splits.

Methylation values were visually compared using boxplots (Tukey, J. W. Exploratory Data Analysis. Reading, Mass.: Addison-Wesley. (1977)). Cross tabulations and logistic regressions were used to determine if methylation of these genes was associated with clinical parameters. Statistical computations were performed using the SAS system and all p-values reported are two sided.

Example 2

Renal Neoplasia Sample Collection and DNA Preparation

Written informed consent was obtained from 26 patients with a renal lesion. Eighteen samples of peripheral blood and twenty-six urine samples were collected before surgical intervention. Overall, seventeen urine and serum DNA samples with matched primary tumor tissue, and nine additional urine sediment samples and one serum sample from these patients were used to determine the clinical sensitivity of the QMSP assay. Neoplastic kidney tissue was obtained immediately after surgical resection and stored at −80° C. Urine from ninety-one age-matched control subjects (median age, 56.5 years; range, 28-84 years) was analysed for the nine genes. Of these ninety-one subjects, nine patients were diagnosed with benign prostate hyperplasia; ten patients harbored atypical cells by urine cytology examination; five had cancer other than of the genitourinary system (1 non-small cell carcinoma of lung, 1 basal cell carcinoma of skin, 1 malignant melanoma of leg, 1 Kaposi's sarcoma of leg, and 1 infiltrating ductal carcinoma of the breast); 1 had fibroepithelial polyp of the bladder; 3 had tubular adenomas of the colon; 1 had organizing thrombus in the vagina; 25 visited the hospital for routine physical examination; 20 had either macroscopic or microscopic hematuria; and 17 had vague urologic symptoms but no malignant condition was detected. Among the ninety-one patients, sixty-six were male and twenty-five were female. Thirty serum samples (15 from smokers and 15 from non-smokers without any history of cancer) from age-matched individuals were collected as controls. Seventeen primary tumors were later collected, and tumor tissues were microdissected as described previously (Hoque et al., Cancer Res, 63: 2216-22, 2003) DNA was obtained from serum, urine, and tumor samples by digestion with 50 μg/ml proteinase K (Boehringer, Mannheim, Germany) in the presence of 1% SDS at 48° C. overnight, followed by phenol/chloroform extraction and ethanol precipitation. Detailed information on these patients is summarized in Table 9.

Example 2

Renal Neoplasia Bisulfite Treatment

DNA from urine sediment was subjected to bisulfite treatment as described above (Herman et al. Proc Natl Acad Sci USA, 93: 9821-6, 1996). Briefly, 2 μg of genomic DNA was denatured in 0.2 M NaOH for 20 minutes at 50° C. The denatured DNA was diluted in 500 μl of a freshly prepared solution of 10 mM hydroquinone and 3 M sodium bisulfite and was incubated for 3 hours at 70° C. After incubation, the DNA sample was desalted through a column (Wizard DNA Clean-Up System; Promega, Madison, Wis.), treated with 0.3 M NaOH for 10 minutes at room temperature, and precipitated with ethanol. The bisulfite-modified genomic DNA was resuspended in 120 μl of $H_2O$ and stored at −80° C.

Example 2

Methylation Analysis

The bisulfite-modified DNA was used as a template for fluorescence-based real-time PCR (Taqman) as described previously (Harden et al., Clin Cancer Res, 9: 1370-5, 2003). In brief, primers and probes were designed to specifically amplify the bisulfite-converted promoter of the gene of interest. These are described in Topaloglu et al., Clin Cancer Res, 10: 2284-8, 2004; Harden et al., Clin Cancer Res, 9: 1370-5, 2003; Eads et al., Cancer Res, 61: 3410-8, 2001; and Eads et al., Nucleic Acids Res, 28: E32 2000). The ratios between the values of the gene of interest and the internal reference gene, β-actin, obtained by Taqman analysis were used as a measure for representing the relative level of methylation in the particular sample (gene of interest/reference gene×1000) as described previously (Eads et al., Nucleic Acids Res, 28: E32 2000; Eads et al., Cancer Res, 59: 2302-6, 1999). Fluorogenic PCRs were carried out in a reaction volume of 20 µl consisting of 600 nM of each primer; 200 of nM probe; 0.75 units of platinum Taq polymerase (Invitrogen, Carlsbad, Calif.); 200 µM each of dATP, dCTP, dGTP, and dTTP; 16.6 mM ammonium sulfate; 67 mM Trizma; 6.7 mM $MgCl_2$ (2.5 mM for p16); 10 mM mercaptoethanol; and 0.1% DMSO. Three µl of treated DNA solution were used in each real-time MSP reaction. Amplifications were carried out in 384-well plates in a 7900 HT Sequence Detection System (Applied Biosystems, Foster City, Calif.). Each plate consisted of patient samples and multiple water blanks and positive and negative controls. Leukocytes from a healthy individual were methylated in vitro with excess SssI methyltransferase (New England Biolabs, Beverly, Mass.) to generate completely methylated DNA, and serial dilutions of this DNA were used for constructing the calibration curves on each plate.

Example 2

Renal Carcinoma Statistical Analysis

All of the statistical tests were performed using Excel software (Microsoft, Redmond, Wash.). The sensitivity of QMSP-based detection of hypermethylation in urine and serum was calculated as number of positive tests/number of cancer cases. The specificity was calculated as number of negative tests/number of cases without genitourinary cancer for urine (and absence of any cancer for serum).

Example 3

Prostate Carcinoma Patients and Sample Collection

Fifty six patients undergoing prostatectomy for prostate adenocarcinoma and 16 patients undergoing cystoprostatectomy for bladder carcinoma at the Johns Hopkins Hospital between November 2001 and May 2002 (Harden et al., J Natl Cancer Inst, 95: 1634-7, 2003) were included in this study. Immediately after resection, sextant biopsies (apex, mid, and base from right and left sides) were taken from all 72 of the resected prostates and kept frozen at −80° C. The biopsies were sectioned to extract DNA with a 5-µm section taken every tenth slice and stained with hematoxylin and eosin for blinded histologic evaluation by an expert uropathologist (J. I. E.). All of the resected prostates were serially sectioned and examined histopathologically. These final pathology results were considered to be the gold standard for the presence of adenocarcinoma.

Example 3

Prostate Carcinoma Bisulfite Treatment

Genomic DNA was extracted and bisulfite modification of genomic DNA was carried out as described previously (Merlo et al., Nat Med, 1: 686-92, 1995). Briefly, 2 µg of DNA in 20 µl of $H_2O$ containing 5 µg of salmon sperm DNA was denatured by incubation with 0.3 M NaOH at 50° C. for 20 minutes. The DNA was then incubated at 70° C. for 3 hours in a 500-µl reaction mixture containing 2.5 M sodium metabisulfite and 0.125 M hydroquinone (pH 5.0). The treated DNA was purified with the Wizard DNA purification system according to the manufacturer's instructions (Promega) and finally resuspended in 100 µl of $H_2O$ after ethanol precipitation.

Example 3

Prostate Carcinoma Quantitative Real-Time Methylation Specific PCR

DNA templates were amplified by fluorescence-based quantitative real-time methylation-specific PCR as described previously (Merlo, supra). Briefly, primers and probes were designed to amplify specifically bisulfite converted DNA at the 5' end of T1G1, APC, RARβ2, GSTP1 and β-actin (used as the internal reference gene). The ratio of the gene of interest to β-actin (multiplied by 1000) for each sample was used as a measure for representing the relative level of methylated DNA for each gene of interest within each sample. The sequences of the primers and probe for T1G1 were 5'-TTTTTCGTCGCGGTTTGG-3' (sense primer) (SEQ ID NO: 31), 6-carboxyfluorescein-TCGGTTTTGCGTTGCG-GAGGC-TAMRA (probe) (SEQ ID NO: 33), and 5'-CGC-TACCCGAACTTAATACTAAAATACG-3' (antisense primer) (SEQ ID NO: 32). Sequences for APC, RARβ2, GSTP1, and β-actin were described previously (Harden et al., J Urol, 169: 1138-42, 2003; and Usadel et al., Cancer Res, 62: 371-S, 2002). Amplifications were carried out in 384-well plates using a 7900 Sequence detector (Perkin-Elmer Applied Biosystems). All of the samples were ran in triplicate, and each plate included multiple water blanks, a negative control, and serial dilutions of a positive control for constructing the calibration curve. Leukocyte DNA from a healthy individual was used as the negative control. The same lymphocyte DNA was methylated in vitro with excess SssI methyltransferase (New England Biolabs, Inc., Beverly, Mass.) to generate completely methylated DNA at all of the CpGs and used as the positive control.

Example 3

Prostate Carcinoma Statistical Analysis

The medians and ranges of the methylation ratios for the samples was determined. Associations between these values were tested by using the Mann-Whitney U test, and P values<0.05 were considered to be significant.

Example 4

Prostate Sample Collection and DNA Preparation

Urine samples of fifty-two patients with prostate cancer who underwent curative surgery at the Johns Hopkins University School of Medicine were evaluated. Detailed data on these patients are listed in Table 11. Urine samples from ninety-one age-matched individuals (median age, 56.5 years; range, 28 to 84 years) without a history of genitourinary malignancy were used as controls. Of these ninety-one individuals, nine were diagnosed with benign prostate hyperplasia, ten harbored atypical cells by urine cytology examination, five had primary cancers in other sites (non-small-cell carcinoma of lung, n=1; basal cell carcinoma of skin, n=1;

malignant melanoma of leg, n=1; Kaposi's sarcoma of the leg, n=1; and infiltrating ductal carcinoma of the breast, n=1), one had fibroepithelial polyp of the bladder, three had tubular adenomas of the colon, one had organizing thrombus in the vagina, twenty-five visited the hospital for routine physical examination, twenty had either macroscopic or microscopic hematuria, and seventeen were seen for vague urologic symptoms without malignancy. Among the ninety-one controls, sixty-six were male, and twenty-five were female. Fifty milliliters of voided urine were collected from all controls and patients before definite surgery. Urine samples were spun at 3,000×g for 10 minutes and washed twice with phosphate-buffered saline. All samples were stored at −80° C. Frozen urine cell pellets were digested with 1% sodium dodecyl sulfate and 50 µg/mL of proteinase K (Boehringer, Mannheim, Germany) at 48° C. overnight, followed by phenol/chloroform-extraction and ethanol precipitation of DNA, as previously described.

Example 4

Bisulfite Treatment

DNA from urine sediment or from primary tumors was subjected to bisulfite treatment, as described previously (Herman et al., Proc Natl Acad Sci USA 93:9821-9826, 1996). Briefly, 2 µg of genomic DNA was denatured in 0.2 M of NaOH for 20 minutes at 50° C. The denatured DNA was diluted in 500 µL of freshly prepared solution of 10 mmol/L hydroquinone and 3 M of sodium bisulfite and incubated for 3 hours at 70° C. After incubation, the DNA sample was desalted through a column (Wizard DNA Clean-Up System, Promega, Madison, Wis.), treated with 0.3 M of NaOH for 10 minutes at room temperature, and precipitated with ethanol. The bisulfite-modified genomic DNA was resuspended in 120 µL of LoTE (EDTA 2.5 mmol/L and Tris-HCl 10 mmol/L) and stored at −80° C.

Example 4

Prostate Carcinoma Methylation Analysis

The bisulfite-modified DNA was used as a template for fluorescence-based real-time polymerase chain reaction (PCR), as previously described (Harden et al., Clin Cancer Res 9:1370-1375, 2003). In brief, primers and probes were designed to specifically amplify the bisulfite-converted promoter of the gene of interest. The ratios between the values of the gene of interest and the internal reference gene, β-actin, which was obtained by Taqman analysis, were used as a measure for representing the relative level of methylation in the particular sample (gene of interest/reference gene×1,000). Fluorogenic PCRs were carried out in a reaction volume of 20 µL consisting of 600 nmol/L of each primer; 200 nM of probe; 0.75 U of platinum Taq polymerase (Invitrogen, Carlsbad, Calif.); 200 µmol/L each of 2'-Deoxyadenosine 5'-triphosphate, 2'Deoxycytidine 5'-triphosphate, 2'-Deoxyguanosine 5'-triphosphate, and 2'-Deoxythymidine 5'-triphosphate; 16.6 mmol/L of ammonium sulfate; 67 mmol/L of Trizma (Sigma, St Louis, Mo.); 6.7 mmol/L of $MgCl_2$ (2.5 mmol/L for p16); 10 mmol/L of mercaptoethanol; and 0.1% dimethylsulfoxide. Three microliters of treated DNA solution were used in each real-time MSP reaction. Amplications were carried out in 384-well plates in a 7900 Sequence Detector System (Perkin-Elmer Applied Biosystems, Norwalk, Conn.). Each plate consisted of patient samples and multiple water blanks, as well as positive and negative controls. Leukocytes from a healthy individual were methylated in vitro with excess SssI methyltransferase (New England Biolabs Inc, Beverly, Mass.) to generate completely methylated DNA, and serial dilutions of this DNA were used for constructing the calibration curves on each plate. Identical lab procedures and intermixing were performed in the same laboratory for each batch tested.

Example 4

Statistical Analysis

First, for all the markers, individual receiver operating characteristic curves were generated. This was performed by sorting the different percent methylation scores and checking for sensitivity and specificity in each unique score of the end point to be tested (cancer v normal samples). The positive likelihood ratio was calculated at each cut point. Then maximal likelihood ratio-positive values for all the different markers were combined, and learning sets were created. In this way, the original continuous and rather complex information in the QMSP data was transformed to a discrete binary read-out. Then, all the learning sets were tested for all possible combinations of markers.

In the cross-validation procedure, the samples were randomly remaining one tenth was used as a test set to calculate performance. The sampling procedure ensured equal class representation in the training set (stratification constraints). This procedure was repeated 10 times by maximizing the chance that each instance was used in the test set. Over the 10 experiments, a general sensitivity and specificity score was computed. Because the procedure was a stochastic, we repeated the procedure multiple times, and as can be expected from a 10-fold cross validation, the computed results were robust.

In the final step, machine learning was applied. This was done by applying orthologous data analysis techniques using the WEKA System's Bayes Network approach (Witten et al., Data Mining: Practical Machine Learning Tools With Java Implementations. Morgan Kaufmann Publishers, San Francisco, Calif., 2000). Orthologous data analysis looks at data from different perspectives and is capable of detecting completely different patterns in datasets (technically independent). It also adds to the interpretability of the results and gives additional information to the learning set and its saturation. All P values were calculated using the $x^2$ test. When observed frequencies were below 5, a Fisher correlation test was performed. All statistical tests were two sided. All differences were considered statistically significant if P≤05. The associations between methylation of an individual gene and clinical and pathologic variables were assessed using logistic regression.

Other Embodiments

From the foregoing description, it will be apparent that variations and modifications may be made to the invention described herein to adapt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for identifying a human subject as having a bladder neoplasia, the method comprising:
   a) obtaining DNA from a first bladder tissue sample from said human subject,
   b) performing bisulfite modification to the DNA in a);
   c) performing quantitative real-time methylation specific PCR (QMSP) on bisulfite modified DNA from the first sample using the PCR primers and probe specific for the promoter region of genes of interest, wherein the genes of interest comprise p16, ARF, MGMT, and GSTP1, and the PCR primers and probe for the promoter region of the genes of interest consist of SEQ ID NOs: 3, 5, 6, 7, 13, 23, 25, 26, and 27;
   d) determining the promoter methylation level of the promoter regions of the genes of interest in the DNA from the first bladder tissue sample of the subject,
   e) providing a reference non-neoplastic bladder tissue sample;
   f) comparing the level of methylation of the promoter region of the genes of interest from the first bladder tissue sample of the subject, to the level of methylation of the promoter region of the genes of interest in the reference non-neoplastic bladder tissue sample; and
   g) identifying said human subject as having a bladder neoplasia when the level of methylation of the promoter region of the genes of interest in the first bladder tissue sample of the subject, is increased relative to the level of methylation of the promoter region of the genes of interest in the reference non-neoplastic bladder tissue sample.

2. The method of claim 1, wherein c) the promoter region of the genes of interest includes at least two or more additional promoter regions of genes of interest selected from the group consisting of: RAR-β2, TIMP3, CDH1, RASSF1A, and APC, and the primers and probe for the promoter region of the genes of interest are selected from the group consisting of SEQ ID NOs: 2, 4, 8, 9, 10, 12, 14, 18, 19, 20, 22, 24, 28, 29, and 30.

3. A method for identifying a human subject as having a bladder neoplasia, the method comprising:
   a) obtaining DNA from a first urine sample from said human subject,
   b) performing bisulfite modification to the DNA in a);
   c) performing quantitative real-time methylation specific PCR (QMSP) on bisulfite modified DNA from the first sample using the PCR primers and probe specific for the promoter region of genes of interest, wherein the genes of interest comprise p16, ARF, MGMT, and GSTP1, and the PCR primers and probe for the promoter region of the genes of interest consist of SEQ ID NOs: 3, 5, 6, 7, 13, 23, 25, 26, and 27;
   d) determining the promoter methylation level of the promoter regions of the genes of interest in the DNA from the first urine sample of the subject,
   e) providing a reference non-neoplastic urine sample;
   f) comparing the level of methylation of the promoter region of the genes of interest from the first urine sample of the subject, to the level of methylation of the promoter region of the genes of interest in the reference non-neoplastic urine sample; and
   g) identifying said human subject as having a bladder neoplasia when the level of methylation of the promoter region of the genes of interest in the first urine sample of the subject, is increased relative to the level of methylation of the promoter region of the genes of interest in the reference non-neoplastic urine sample.

4. The method of claim 3, wherein c) the promoter region of the genes of interest includes at least two or more additional promoter regions of genes of interest selected from the group consisting of: RAR-β2, TIMP3, CDH1, RASSF1A, and APC, and the primers and probe for the promoter region of the genes of interest are selected from the group consisting of SEQ ID NOs: 2, 4, 8, 9, 10, 12, 14, 18, 19, 20, 22, 24, 28, 29, and 30.

5. The method of claim 1, wherein in c) the promoter region of the genes of interest includes at least one or more additional promoter regions of genes of interest selected from the group consisting of: TIMP3, CDH1, RASSF1A, and APC, and the primers and probe for the promoter region of the genes of interest are selected from the group consisting of SEQ ID NOs: 2, 4, 9, 10, 12, 14, 19, 20, 22, 24, 29, and 30.

6. The method of claim 3, wherein in c) the promoter region of the genes of interest includes at least one or more additional promoter regions of genes of interest selected from the group consisting of: TIMP3, CDH1, RASSF1A, and APC, and the primers and probe for the promoter region of the genes of interest are selected from the group consisting of SEQ ID NOs: 2, 4, 9, 10, 12, 14, 19, 20, 22, 24, 29, and 30.

* * * * *

SEQUENCE LISTING

<160> NUMBER OF SEQ ID NOS: 33

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tggtgatgga ggaggtttag taagt                                             25

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gaaccaaaac gctccccat                                                    19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acgggcgttt tcggtagtt                                                    19

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aattttaggt tagagggtta tcgcgt                                            26

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agttgcgcgg cgatttc                                                      17

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgaatatact aaaacaaccc gcg                                      23

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttattagagg gtgggcgga tcgc                                      24

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gggattagaa tttttatgc gagttgt                                   27

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcgttgaagt cggggttc                                            18

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcgtcggagg ttaaggttgt t                                        21

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
accaccaccc aacacacaat aacaaacaca                               30

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
cccgtcgaaa acccgccgat ta                                                    22

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
cgactctaaa ccctacgcac gcgaaa                                                26

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
cgcccacccg acctcgcat                                                        19

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
cggtcgacgt tcggggtgta gcg                                                   23

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
aatcctcgcg atacgcaccg tttacg                                                26

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
agtagtatgg agtcggcggc ggg                                                   23

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
tgtcgagaac gcgagcgatt cg                                                    22

```
<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
acaaacgcga accgaacgaa acca                                              24

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
aactcgctcg cccgccgaa                                                    19

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aaccaataaa acctactcct cccttaa                                           27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ttatatgtcg gttacgtgcg tttatat                                           27

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccgaacctcc aaaatctcga                                                   20

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tccccaaaac gaaactaacg ac                                                22
```

-continued

```
<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gccccaatac taaatcacga cg                                          22

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26 gtatttttc gggagcgagg c                                            21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gaccccgaac cgcgaccgta a                                           21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
taccccgacg atacccaaac                                             20

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cccgtacttc gctaactta aacg                                         24

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctctccaaaa ttaccgtacg cg                                          22

<210> SEQ ID NO 31
<211> LENGTH: 18
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tttttcgtcg cggtttgg                                                   18

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cgctacccga acttaatact aaaatacg                                        28

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tcggttttgc gttgcggagg c                                               21
```